US012678526B2

(12) United States Patent
Lloyd

(10) Patent No.: US 12,678,526 B2
(45) Date of Patent: Jul. 14, 2026

(54) SYSTEMS AND METHODS FOR DISINFECTING PLUMBING FIXTURES AND ROOMS WITH PLUMBING FIXTURES

(71) Applicant: Ralph Birchard Lloyd, Fayetteville, NC (US)

(72) Inventor: Ralph Birchard Lloyd, Fayetteville, NC (US)

( * ) Notice: Subject to any disclaimer, the term of this patent is extended or adjusted under 35 U.S.C. 154(b) by 768 days.

(21) Appl. No.: 18/091,479

(22) Filed: Dec. 30, 2022

(65) Prior Publication Data

US 2023/0211030 A1 Jul. 6, 2023

Related U.S. Application Data

(60) Provisional application No. 63/295,836, filed on Dec. 31, 2021, provisional application No. 63/317,238, filed on Mar. 7, 2022, provisional application No. 63/334,130, filed on Apr. 23, 2022, provisional application No. 63/339,453, filed on May 7, 2022.

(51) Int. Cl.
| | |
|---|---|
| *A61L 2/00* | (2006.01) |
| *A61L 2/10* | (2006.01) |
| *A61L 2/183* | (2026.01) |
| *A61L 2/22* | (2006.01) |
| *A61L 2/24* | (2006.01) |
| *A61L 9/00* | (2006.01) |
| *A61L 103/75* | (2026.01) |

(52) U.S. Cl.
CPC ................. *A61L 2/183* (2013.01); *A61L 2/10* (2013.01); *A61L 2/22* (2013.01); *A61L 2/24* (2013.01); *A61L 2103/75* (2026.01); *A61L 2202/14* (2013.01); *A61L 2202/15* (2013.01)

(58) Field of Classification Search
CPC ... A61L 2/183; A61L 2/22; A61L 2/24; A61L 2/10; A61L 2202/14; A61L 2202/15; C02F 1/78; B01F 3/04503
USPC ..................................... 422/28, 30, 292, 305
See application file for complete search history.

(56) References Cited

U.S. PATENT DOCUMENTS

| | | | |
|---|---|---|---|
| 8,551,399 B2 * | 10/2013 | Shannon | ................. A61L 2/202 |
| | | | 422/28 |
| 8,668,883 B2 * | 3/2014 | Garner | ................... B01D 53/72 |
| | | | 96/108 |
| 2017/0096336 A1 * | 4/2017 | Lynn | .................... C11D 3/2093 |

* cited by examiner

*Primary Examiner* — Monzer R Chorbaji
(74) *Attorney, Agent, or Firm* — Ashley D. Johnson; Dogwood Patent and Trademark Law

(57) ABSTRACT

The invention is a system and method for the initial and on-going disinfection of pathogens from building surfaces and plumbing fixtures. The disclosed system and method can be particularly useful in bathrooms to disinfect the drains of sinks, toilets, bathtubs, and other standing water sources that act as persistent reservoirs of deadly pathogens. The disclosed system and method include a disinfecting chemical storage or disinfecting chemical generation unit, a control module, a conduit configured to pump or convey the disinfecting fluid to a surface of the plumbing fixture, an attachment configured to attach a portion of the distribution structure piping, and at least two separate openings in the piping or other conduit.

20 Claims, 5 Drawing Sheets

SYSTEMS AND METHODS FOR DISINFECTING PLUMBING FIXTURES AND ROOMS WITH PLUMBING FIXTURES

CROSS-REFERENCE TO RELATED APPLICATIONS

The current application claims priority to U.S. Provisional Patent Application Nos. 63/295,836, 63/317,238, 63/334, 130, and 63/339,453 filed Dec. 31, 2021, Mar. 7, 2022, Apr. 23, 2022, and May 7, 2022, respectively, the entire contents of which are incorporated by reference herein.

TECHNICAL FIELD

The presently disclosed subject matter is generally directed to systems and methods for disinfecting plumbing fixtures, such as sinks, toilets, bathtubs, showers, and rooms with floor drains, and the air and other surfaces in rooms with plumbing fixtures.

BACKGROUND

The presently disclosed subject matter relates generally to systems and methods for disinfecting the interior of buildings, including the building walls, floors, and items included in the buildings (e.g., bathroom walls and floors). The disclosed system and methods can have particular application with plumbing fixtures found in food processing and preparation facilities and bathrooms (such as sinks, toilets, and showers) and the water supply and drain piping associated with such fixtures. The need for proper disinfection is tantamount, as deadly pathogens are known to colonize toilets, sinks, shower drains, and other bathroom fixtures and surfaces. Proper disinfection of surfaces and plumbing fixtures is thus of ongoing importance in food processing plants and food preparation facilities (such as restaurants).

In April of 2019, the New York Times reported that a deadly strain of the fungus *Candida auris* that killed 50% of infected patients within 90 days had become resistant to antifungal treatments. The strain was found to be present in hospitals in New York, Illinois, and New Jersey. In one hospital room of an infected patient, the fungus was detected on all surfaces tested, in drains, on equipment, and floor and ceiling tiles. An estimated 75,000 people die annually from infections contracted in hospitals in the US alone, and four times this number die annually in US nursing homes from infections.

Antibiotic-resistant and antifungal-resistant pathogens are increasing in number, and new systems and methods are required to eradicate these organisms from health care and other facilities and prevent them from colonizing surfaces, equipment, and fixtures throughout the facility. It has been reported that disinfected sinks can be re-contaminated by pathogens that have colonized the sink drains. One researcher reported contaminants can re-emerge from a sink drain upwards into a sink basin at a rate measured in inches per day. Accordingly, there is a need in the art for permanently removing pathogens from sinks and other plumbing fixtures.

Occasionally there are systems and methods in the prior art that apply a limited number of the concepts disclosed in the present system and method, but these are not without significant shortcomings, shortcomings which the present system and method successfully resolve. For example, PrescientX, a company in Cambridge, ON, markets a sink the call the SmartFLO3 Hand Hygiene Sink. The sink comprises one water outlet that apparently is activated when a user, wanting to wash their hands, comes in proximity to the sink. Water comprising dissolved ozone and other reactive oxygen species, it is claimed, is then discharged onto a user's hands for hand washing. It is a no-touch system, with no faucet handles, and no provision is made for adjusting the temperature to the user's preference. In addition to emitting water for washing a user's hands, the control system periodically and automatically dispenses water out of the single water discharge port, which flows onto a spot on the basin of the sink and runs down the drain. The company claims that with periodic and automatic emissions of ozonated water, the microorganisms in the drain can be controlled and kept from creeping back up onto the sink bowl surfaces and contaminating them.

This is a step in the right direction, but the limitations of this design are significant. First, an entire sink must be purchased and installed, a significant upfront cost to users, and no provision is made with this product to retrofit an existing sink. Second, there is no temperature control of the water being emitted. Third, the sink has limited usefulness for purposes beyond hand washing. Fourth, the sink only emits water comprising disinfecting chemicals. If a healthcare worker or patient wanted to wash their face or hands or perform some other task in water without the disinfecting chemical present, they could not do so. Fifth, not all surfaces of the sink are disinfected with the ozonated water, because the ozonated water follows a defined path into the sink basin and runs immediately down the drain. Based on their sales literature, it appears that the disinfecting fluid only contacts about one fourth to one third of the surfaces of the sink basin. The only way for the back and sides of the sink to be disinfected is if a person were to purposely interrupt the flow of water and splash it manually around the walls of the sink. Indeed, the primary purposes of the device according to the manufacturer is to disinfect the sink drain and the hands of persons, not the majority of the sink surfaces. Sixth, ozone is the only disinfectant offered. If a customer was concerned about ozone getting into the air and causing an inhalation hazard for users, there is no alternative to provide a system with a different disinfecting chemical. Seventh, the system is not amenable to other plumbing fixtures such as a bathtub, a shower, a toilet, or larger sinks used for any purpose other than washing hands. Eighth, other surfaces in the bathroom or room in which the SmartFLO3 system is installed will not be disinfected. Ninth, there is no system to remove or destroy ozone vapors to ensure the safety of persons in the area. Tenth, PrecientX's SmartFLO3 only disinfects one sink and drain and is not amenable to disinfecting multiple plumbing fixtures or multiple sinks from a single disinfecting fluid delivery system. To disinfect multiple sinks, one would have to purchase and install multiple SmartFLO3 sink systems. Eleventh, the SmartFLO3 sink with built-in disinfecting system apparently only comes in one size, shape, style, and color. Twelfth, it appears that PrecientX is using an electrolyzer in their device for making ozone. Electrolyzers generating ozone are known to be limited in the concentration of ozone in the water they are able to produce, typically around 1.5 ppm ozone in water. However, when ozone is generated in a gas from oxygen, it can be made at high enough concentrations such that after being combined with water, the resultant ozone concentration in the water may be significantly higher, for example above 2 ppm, 3 ppm, 4 ppm, or even above 5 ppm, and higher concentrations are more effective at killing microorganisms. The present invention allows for making ozonated water at these higher concentrations by conventional means then transferring that water to plumbing fixtures through distribution structures to disinfect plumbing fixture surfaces. Various embodiments of the present system and method address all of the shortcomings of PrecientX's products.

PrescientX also offers a system called OzoFlo which is apparently an ozone generating faucet attachment intended to connect to an existing cold water supply line on an existing faucet, apparently replacing the normal cold water control handle and cold water supply faucet. Like the SmartFLO3 sink, the OzoFlo attachment is intended to be used for hand washing, and the attachment may also periodically dispense ozonated water into the sink to control pathogens in the drain. Since the OzoFlo system replaces the cold-water supply line of the faucet, the user loses the temperature adjustment features of a typical faucet when hot and cold water can be mixed, and the user is left with the choice of hot water at full temperature or cold ozonated water, but not the two mixed together. Although OzoFlo solves the problem of not requiring the installation of a new sink, almost all of the other problems noted previously for the SmartFLO3 system still remain unsolved with the Ozo-Flo solution, problems that the present system and method solve. For example, the present system and method can disinfect a plumbing fixture with standard hot and cold water faucets, and it need not replace or take away an existing water supply line to a plumbing fixture as does PrecientX's OzoFlo solution.

SUMMARY

In some embodiments, the presently disclosed subject matter is directed to a system for disinfecting at least one plumbing fixture. Particularly, the system comprises at least one plumbing fixture located in a room comprising a bathroom in a building. The system also includes a disinfecting chemical storage or disinfecting chemical generation unit for storing, generating, or both storing and generating a disinfecting fluid. The system further includes a programmable control module or manual controls for inputting, adjusting, or both inputting and adjusting system control parameters. The system comprises a distribution structure comprising piping or other conduit configured to pump or convey the disinfecting fluid to a surface of the plumbing fixture. The system comprises an attachment configured to attach a portion of the distribution structure piping or other conduit on, in, or near the plumbing fixture. The system includes at least two separate openings in the piping or other conduit, wherein each of the at least two separate openings is configured to distribute the disinfecting fluid onto a different area on a surface of the plumbing fixture surface relative to the remaining openings.

In some embodiments, the system comprises at least three, four, five, six, seven, eight, nine, or ten openings.

In some embodiments, the plumbing fixture is selected from a sink, a toilet, a bathtub, a shower, or a portion of a wall or floor of the room equipped with a floor drain.

In some embodiments, the system is configured to disinfect either simultaneously or sequentially two or more plumbing fixtures wherein the two or more plumbing fixtures are the same type of plumbing fixture or are different types of plumbing fixtures.

In some embodiments, a portion of the distribution structure is positioned into a new plumbing fixture.

In some embodiments, a portion of the distribution structure is configured to apply the disinfecting fluid onto at least one faucet, handle, or other high touch point of the at least one plumbing fixture.

In some embodiments, the system further includes a backsplash or other barrier to control the direction of flow of the disinfecting fluid and to prevent the disinfecting fluid from contacting non-plumbing fixture surfaces or surfaces of the at least one plumbing fixture not intended to be regularly wetted with fluids.

In some embodiments, a portion of the distribution structure is configured to apply the disinfecting fluid onto at least 10%, 20%, 30%, 40%, 50%, 60%, 70%, 80%, or 90% of a surface of the at least one plumbing fixture intended to be regularly wetted with fluids.

In some embodiments, the disinfecting fluid comprises ozone.

In some embodiments, the disinfecting chemical storage unit stores a disinfecting chemical chosen from hydrogen peroxide, a chemical comprising chlorine, or a chemical comprising a quaternary ammonium compound.

In some embodiments, the presently disclosed subject matter is directed to a healthcare facility, nursing home, rehabilitation or long-term care facility, restaurant, office building, school, retail store, hotel, hospitality facility, auditorium, theater, recreational facility including a gymnasium, stadium, swimming pool, fitness center, food processing or preparation facility, research facility, manufacturing facility, private restroom, or public restroom comprising the disclosed system for disinfecting at least one plumbing fixture.

In some embodiments, the system further comprises at least one germicidal radiation emitter including a UV emitter.

In some embodiments, the system further comprises a person detection sensor, a door position detection sensor, or both.

In some embodiments, the system includes a plurality of germicidal radiation emitters wherein each of the germicidal radiation emitters are located at least one, two, three, four, five, six, eight, or ten feet apart from another germicidal radiation emitter.

In some embodiments, the system further includes an air movement element configured to move air in the room, the air movement element comprising an air filter equipped with a fan to circulate air through the air filter.

In some embodiments, the system further includes a compound for absorbing or destroying an airborne disinfecting chemical, including ozone, a sensor to detect compounds in the air, including a disinfecting chemical, or both.

In some embodiments, the system includes a programmable control module configured to control components of the air movement element, the germicidal radiation emitter, the distribution structure, the air filter, or combinations thereof.

In some embodiments, a portion of the distribution structure is configured to apply the disinfecting fluid onto a toilet seat.

In some embodiments, the system includes an air movement element configured to move air onto a toilet seat.

DETAILED DESCRIPTION

Figures 1A, 1B:
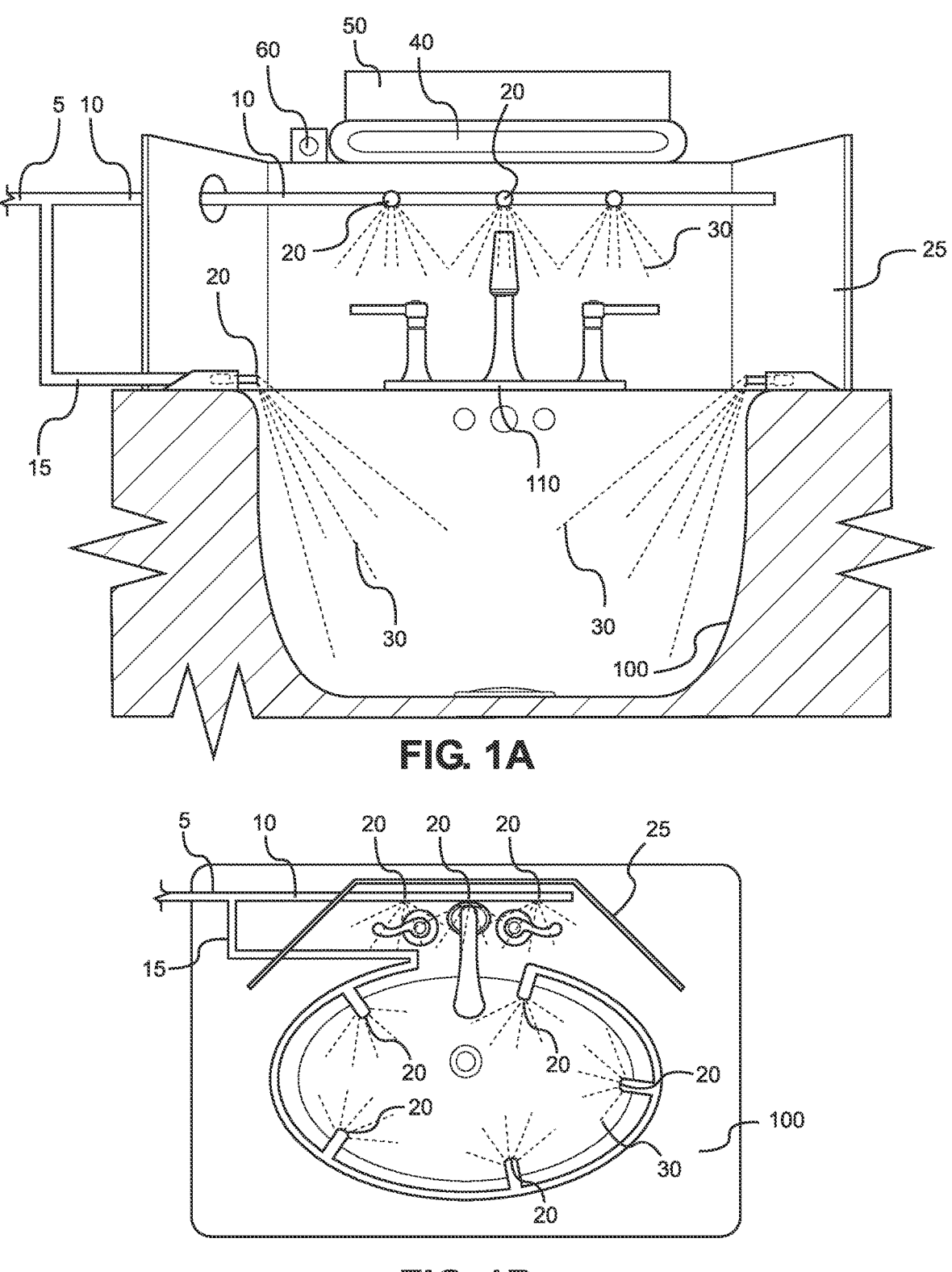
FIG. 1a is a front plan view of a disinfecting fluid delivery system in accordance with some embodiments of the presently disclosed subject matter.
FIG. 1b is a top plan view of a disinfecting fluid delivery system in accordance with some embodiments of the presently disclosed subject matter.

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

As used herein, the term "and/or" includes any and all combinations of one or more of the associated listed items.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

The presently disclosed subject matter is directed to systems and methods for the initial and on-going disinfection of pathogens from building surfaces and plumbing fixtures. The disclosed systems and methods can be particularly useful in bathrooms to disinfect the drains of sinks, toilets, bathtubs, and other standing water sources that act as persistent reservoirs of deadly pathogens. As used herein, the term "disinfect" or "disinfection" refers to the partial destruction or inactivating of a population of microorganisms, such as viruses, bacteria, fungi, etc. The term "sterilize" or "sterilization" refers to the achievement of extremely high or total levels of destruction or inactivation of microorganisms. Although the disclosed systems and methods can in some instances achieve sterilization as described below, it is the intention of the disclosed systems and methods to destroy a significant percentage (e.g., greater than 50%, 60%, 70%, 80%, 90%, 95%, 99% or more) of microorganisms in a plumbing fixture, surface, or other application. As a result, the microorganisms are less likely to infect objects or persons in the vicinity of the plumbing fixture or area (e.g., bathroom). The term "microorganism" refers to living organisms that are small in size (visible only with the aid of a microscope), such as bacteria, yeast, protozoa, algae, parasites, viruses, nematodes, and the like. The term "pathogen" refers to a microorganism capable of causing a disease or disease symptoms in an infected subject. It is known that persons can contract deadly pathogens from sinks that harbor pathogens (e.g., splashing of water onto contaminated sink surfaces, contact with the eyes, nose, mouth, or wounds of a person using the sink).

Disinfecting plumbing fixtures (e.g., sinks and toilets) is extremely challenging due to the presence of biofilms (e.g., aggregates of microorganisms) that attach to surfaces and function to protect microorganisms from disinfecting chemicals and agents. The presently disclosed subject matter can disinfect objects and surfaces (including sinks, toilets, showers, other plumbing fixtures, wetted surfaces, and their associated piping systems) to destroy at least about 50-99.999% of the microorganisms on or near the fixtures or surfaces. Thus, the disclosed systems and methods can disinfect at least about (or no more than about) 50%, 60%, 70%, 80%, 90%, 95%, 99%, 99.9%, 99.99%, 99.999%, or more of the microorganisms on a surface or object. In some embodiments, the disclosed systems and methods can reduce the population of microorganisms enough so that the likelihood of those microorganisms being able to be transmitted to persons or objects is reduced by at least 50-90% (e.g., at least/no more than about 50%, 75%, or 90% or more). In some embodiments, the disclosed system and method can keep microorganisms on the fixtures and surfaces disinfected on an ongoing basis so that they do not grow back in appreciable numbers from drain systems so as to re-contaminate the plumbing fixture to the point where it again becomes a vector for transmitting enough pathogens to persons or objects so as to cause disease.

The present system and method provide for a system for disinfecting a plumbing fixture, the system comprising first, a plumbing fixture located in a room in a building, including a bathroom; second, a system for storing or generating a disinfecting chemical; third, a programmable control module or manual controls that allows the user to input or adjust system control parameters such as disinfecting fluid flow rates, dispensing times and durations, including the ability to set each plumbing fixture with its own flow or time or durations or other factors independently of a different plumbing fixture served by the same disinfecting fluid system; fourth, a distribution system comprising piping or other conduit for pumping or otherwise conveying disinfecting fluid to a surface of the plumbing fixture; fifth, a mechanism to attach a portion of the distribution system comprising piping or other conduit on, in, or near the plumbing fixture; sixth, at least two openings in the piping or other conduit, the openings being configured to distribute disinfecting fluid onto at least two different places on a plumbing fixture surface, wherein the openings may comprise a hole of any shape or size, including a slit, or a spray nozzle, and wherein the number of openings may be any number greater than one so as to spread disinfecting fluid onto more areas of the plumbing fixture surface than would be able to be covered by just one opening. The system may also be configured to disinfect either simultaneously or sequentially one or more than one plumbing fixture chosen from a sink, a toilet, a bathtub, a shower, or a portion of a wall or floor of a room equipped with a floor drain, wherein the one or more plumbing fixtures may be of the same type or a different type.

A portion of the distribution system may be configured to be placed onto or near an existing plumbing fixture, or it may be built into a new plumbing fixture, such as flow channels and fluid openings built into a sink, for example. For new sinks with built in fluid channels, the disinfecting fluid distribution system may be much less obtrusive and more aesthetically pleasing. The system for disinfecting a plumbing fixture may provide for a portion of the distribution system to be configured to apply disinfecting fluid onto the faucets or handles or other high touch points of a plumbing fixture such as the faucets and handles of a sink or shower. A backsplash or other barrier may be provided to control the direction of flow of disinfecting fluid, including to prevent the disinfecting fluid from contacting non-plumbing fixture surfaces or surfaces of the plumbing fixture not intended to be regularly wetted with fluids. Systems of the prior art do not have as their goal to disinfect a substantial amount of the wetted surfaces of a plumbing fixture, whereas the system and method of the present invention is configured to apply disinfecting fluid onto at least 10%, or 20%, or 30%, or 40%, or 50%, or 60%, or 70%, or 80%, or 90% of the surfaces of the plumbing fixture intended to be regularly wetted with fluids. The system and method of the present invention may generate a disinfecting chemical on-site, such as ozone, thus saving the expense and logistical burden of bringing into the facility chemicals and loading them into a storage container. Or the invention provides for bringing in chemicals and loading them into a storage container, including hydrogen peroxide, a chemical comprising chlorine, or a chemical comprising a quaternary ammonium compound, but not intending to limit the invention to these disinfecting chemicals.

The system for disinfecting a plumbing fixture may be installed in a healthcare facility, nursing home, rehabilitation or long-term care facility, restaurant, office building, school, retail store, hotel, hospitality facility, auditorium, theater, recreational facility including a gymnasium, stadium, swimming pool, fitness center, food processing or preparation facility, research facility, manufacturing facility, private restroom, or public restroom, or in a home, or in any type of building comprising a plumbing fixture.

In some embodiments, the system and method for disinfecting a plumbing fixture is combined with a system and method for no touch disinfecting of surfaces, such as a germicidal radiation emitter such as a UV emitter, both installed in the same room and in some embodiments controlled by the same control system. In this manner, the UV radiation may disinfect the air and surfaces not being contacted by the disinfecting fluid. Ideally, the germicidal radiation emitting system further comprises a person detection sensor such as a motion detector and a door position detection sensor to ensure that no one is in the room and the door to the outside is closed before emitting potentially harmful levels of germicidal radiation into the room. In some embodiments, a plurality of germicidal radiation emitters are used and located at various points around the room so as to more thoroughly disinfect the room and expose surfaces that otherwise may be in shadows. To accomplish this best, at least two of the plurality of emitters should be located at least one, or at least two, or at least three, or at least four, or at least five, or at least six, or at least eight, or at least ten feet apart.

In some embodiments of the present system and method, the disinfecting of plumbing fixtures using disinfecting chemicals may be augmented with air filtration to help purify the air and in some embodiments help remove disinfecting chemicals and odors and other unwanted airborne pollutants from the air. This may be accomplished using an air filtration device comprising a fan or air moving device which is capable of moving air through a filter. In other embodiments, the air moving device moves air through a chamber comprising a material to absorb or react with or otherwise remove chemicals, including odor causing chemicals and disinfecting chemicals, from the air, including ozone. Activated carbon can remove ozone and other chemicals from the air and is a common absorbent used with air filtration systems. In some embodiments, sensors such as chemical sensors are installed in the room and in communication with the control module, the control module being programmed to turn on or up the circulation of air through the filter or absorbent upon determining the level of chemical in the air is higher than desired. In still other embodiments, a system for disinfecting a plumbing fixture with disinfecting chemicals is augmented by both disinfecting germicidal radiation and an air purifying or air circulating system, which can all be controlled by the same programmable control system.

The present systems and methods provide for disinfecting sinks, bathtubs, toilets, showers, and other plumbing fixtures that often have drain connections leading to sewer or discharge collection systems. The scope of the present invention can include (but is not limited to) bathroom sinks, sinks associated with janitorial cleaning, sinks installed for washing hands prior to surgery or medical exams or procedures, sinks associated with patient rooms or adjacent patient bathrooms in hospitals or nursing homes, sinks used in food processing plants (such as meat packaging facilities), sinks used in restaurants and other food preparation areas, sinks in homes, sinks in public buildings or office buildings, sinks in public restrooms, and/or any sinks installed for any purpose in any building or indoor or outdoor facility. In addition to sinks, the presently disclosed subject matter is applicable to bathtubs and wash facilities of any kind, including bathtubs, showers, poultry or other meat washing facilities, and any type of facility where the cleaning or washing of a person or food or any other object is performed and where the control of pathogens in the washing basin or washing area is desired.

In the following descriptions, sinks, toilets, bathtubs, and showers are primarily used as plumbing fixture examples. However, it will be recognized that the disclosed systems and methods are applicable to a wide variety of plumbing fixtures used for all types of purposes, including facilities used for washing hands, persons, and food. The presently disclosed subject matter is also applicable to specialty toilets, although additional features specifically useful for toilets are also envisioned and described herein. Rooms with floor drains are also examples of plumbing fixtures intended to be disinfected according to the present system and method, such rooms commonly found in locker rooms, group shower areas, bathrooms, or kitchens in restaurants that are designed to be washed down; in these types of plumbing fixtures, often a wall or walls of the room are tiled or have other water proof coverings on the wall and floor to allow for washing down the walls and floor.

The present system and method also provide for automated continuous or semi-continuous disinfection of sinks and plumbing fixtures. In some embodiments, the disclosed systems and methods can be used to disinfect a sink or other washing facility periodically and automatically, by using an electronic control system wherein users can input control parameters such as the disinfecting fluid dispensing duration and time between dispensing events independently for each plumbing fixture.

The term "disinfecting chemicals" can include any chemical species that has the potential to kill pathogens (e.g., any bacteria, virus, fungi, nematode, or unicellular or multicellular organism that has the potential to be harmful to humans or animals). Suitable disinfecting chemicals can include (but are not limited to) hydrogen peroxide, chlorine (Cl2) and other molecules comprising chlorine atoms such as sodium hypochlorite (NaClO), quaternary ammonium compounds, and ozone including ozone dissolved in water. Many other disinfection chemicals and processes known in the art are described in CDC's "Guidelines for Disinfection and Sterilization in Healthcare Facilities" (W. A. Rutala and D. J. Weber, 2008), the entire disclosure of which is hereby incorporated by reference herein. Any of the chemicals and disinfection methods described in the reference above or any chemical or method or combinations of chemicals and methods for disinfection known in the art have applicability to the disclosed system and method.

In some embodiments, ozone can be used as a disinfecting chemical. Ozone is well known disinfectant and has been used to disinfect drinking water, water used for laundering, cooling tower water, ground water, and many other applications known in the art. Ozone can be used in a gaseous form (e.g., mixed with other gases, usually oxygen and nitrogen or air), in an aqueous form (dissolved into or mixed or combined with water), or in other liquid form (dissolved into or mixed with a non-aqueous chemical). For example, ozone can be combined with air and water. Ozone can be created in a variety of ways, such as corona discharge applied to air or oxygen, application of UV radiation to oxygen molecules, or direct electrochemical hydrolysis of water. The presently disclosed subject matter includes any method for generating ozone. Unlike most other disinfecting chemicals, ozone will decay back to oxygen after it is generated, and therefore it is necessary to use it for the purposes of disinfection relatively shortly after generation. Advantageously, ozone can be generated at the point of use and leaves no chemical residue. Thus, ozone greatly reduces the logistical cost burden associated with other disinfecting chemicals, and it minimizes any concerns about residues and disposal of disinfecting chemicals.

For example, disinfecting chemicals may be stored near the sinks and other plumbing fixtures in suitable containers. Alternatively, the chemicals may be stored in a more remote location and pumped to the point of use using suitable tubing or piping distribution system, also referred to as a distribution structure, such distribution system being useful when multiple sinks or plumbing fixtures in various rooms or locations are being disinfected. For example, a disinfecting chemical header or piping system can be run in a ceiling area of a hospital ward, such as an ICU ward or in a nursing home. At each bathroom, sink, patient's room, patient's bathroom, and/or sink area, a branch of tubing or piping can be taken from the header and brought through the ceiling, wall, and/or floor to the sink or other plumbing fixture. A device capable of moving the disinfecting fluid to the plumbing fixture can be provided as are readily available in the art, such as a pump, or the application of air or gas pressure to the fluid storage container, or the locating of the disinfecting chemical storage container at a higher elevation than the plumbing fixture so that the fluid can flow by gravity, or combinations of the above.

In some embodiments, the disinfecting fluid or chemical can be continuously or periodically sprayed onto the plumbing fixture. In the case of a sink, a disinfecting fluid pump may push disinfecting fluid through tubing and out a nozzle that sprays disinfecting fluid into the sink and/or onto the sink facets and handles, such that the disinfecting fluid is collected mainly into the sink basin. In some embodiments, a spray or mist can be applied to thoroughly coat the sink facets, handles, and/or sink basin surface with disinfecting fluid by a single nozzle, or the fluid supply lines may be configured in such a way to provide disinfecting fluid supply to multiple nozzles so as to apply disinfecting fluid onto multiple surfaces or areas of the plumbing fixture. The supply tubing and nozzles can be mounted on a wall near the sink or plumbing fixture, suspended above it, mounted on the fixture or the faucets and handles, mounted on a counter or floor near the plumbing fixture, hung from a ceiling, etc. The fluid supply tubing and nozzle can be oriented to spray disinfecting fluid up into a faucet or shower head or other water dispensing device to disinfect pathogens that may be harbored on the faucet discharge nozzle itself.

The disinfecting chemical can be collected in the sink and/or other plumbing fixture drain system to disinfect the drain. Some of the dispensed fluid may be dispensed onto the floor or walls (intentionally or unintentionally) where it can be collected in a room drain system, useful for disinfecting the room drain system. The walls or floor can be constructed to withstand contact with water and chemicals, common in many bathrooms, shower stalls and shower rooms, locker rooms, food processing areas, and food preparation areas where the walls and floor are tiled or made of other waterproof materials. The fluid dispensing tubing and nozzles may be installed aftermarket (after the sink or plumbing fixture or room has been installed) or the sink or shower or room or new plumbing fixture may be designed with disinfecting fluid channels and openings or spray nozzles built in to facilitate maximum disinfecting and improved esthetics. If the new plumbing fixture is a toilet, multiple spray nozzles can be arranged around the inside of the toilet bowl and oriented to maximize the distribution of disinfecting fluid, including up and under the inside rim of the toilet. In the case of a new bathtub or shower, the fluid dispensing tubing and nozzles can likewise be arranged to disinfect the faucet handles and shower head and any inside or outside surfaces desired.

The disinfecting fluids may also be applied to the outer surfaces of the fixture, such as sprayed onto the outer surfaces of a sink or toilet or bathtub, or onto a toilet seat. The outer surface cleaning can be especially applicable to situations where there is a drain in the floor into which the disinfecting fluid can drain. If the bathroom or room has walls and flooring designed for being wet a majority of the time (such as tiled walls and floors), then the application of the disinfecting fluids can be extended to include spraying disinfecting fluid on the walls and floors. The application can be done automatically on a continuous basis, automatically on a periodic basis (for example once every hour for a one minute duration), or it can be manually activated by personnel (such as a health care worker or restaurant employee) at a convenient time when no one is using the bathroom. In some embodiments, the system may be programmed to dispense fluid onto fixtures at night, after the facility has closed.

As set forth above, in some embodiments ozone can be used as the disinfecting chemical. Ozone can be generated and then dissolved in water at a central location, prior to being pumped through the fluid distribution header and then to the various points of use. Alternatively, localized or distributed ozone generators can be located in for example each bathroom or near each plumbing fixture to be disinfected, and water from the water distribution system already in place or a new water distribution system specifically designed to feed water to the distributed ozone generators may be employed to feed the system that incorporates ozone into water. In instances where existing water supplies are tapped into using known methods, a gaseous ozone generator may be provided with output that feeds into and mixes with the water, as is known in the art. For example, the ozone gas can be fed into the low pressure point of a venturi type device through which the water is pumped. The resultant ozonated water can then be fed to the fixtures as set forth herein. When the ozone gas generator(s) are localized near the point of use, the concentration of the ozone can be better ensured, which is important since ozone will spontaneously decay back into oxygen if not used quickly. In some embodiments, ozone can be generated by electrolyzing water directly, but typically such ozone-generating electrolyzers require purified water to attain longer operating life, as impurities in typical tap water can over time cause the components of the electrolyzer to fail. In some embodiments, a purified water supply header can be provided that feeds purified water to each bathroom or use point along the distribution header, the header then feeding electrolyzers that create ozonated water near a plumbing fixture.

An automated system of the present invention using ozone has several key advantages over other disinfection fluid systems. First, the ozone can be generated from electricity at the point of use, even in the bathroom or very close to the plumbing fixture to be disinfected. As a result, the cost of chemicals, the logistics of handling chemicals, the cost of associated storage tanks and feed systems, and concerns about residues and disposal of chemicals are reduced or eliminated. In addition, ozone is extremely effective at killing pathogens, better than most chemicals, with an oxidation potential of ozone (2.07 eV) being higher than chlorine (1.36 eV) or hydrogen peroxide (1.77 eV). Ozone can further be employed in a gas phase or a water phase for more thorough decontamination of the cracks and crevices of the fixtures. Over time, ozone decays back to oxygen, and no permanent residues or waste disposal concerns arise with ozone. The decay of ozone back to oxygen can be accelerated by bringing it into contact with certain materials or by applying certain wavelengths of UV radiation, as is known in the art.

However, the use of ozone presents several complexities and difficulties, all of which the present invention overcomes. For example, ozone in air presents a significant inhalation health hazard, and ozone concentrations must be limited to 0.1 ppm or less when persons are present. There are no known limitations on ozone concentrations in water, even water comprising ozone which comes in contact with a person's skin.

Accordingly, the presently disclosed subject matter can include a system for generating ozone. One supplier of ozone generating systems is Oxidation Technologies, LLC, located in Inwood, IA. This supplier exhibits many different products on their website for generating and measuring ozone, and the products come in many different and customizable capacities and configurations ranging from outputs of less than one gram/hour of ozone up to 1000 g/h. The predominant technology for generating ozone is corona discharge, but systems that create ozone using 100-240 nm UV radiation and electrolysis, especially for smaller quantities, are also known and manufactured in the art. If small quantities of ozone are desired (up to a few grams per hour), small units or hand-held ozone generators can be used. Direct electrolysis of water may be desired for use directly to spray onto any surface or add to the drain system. However, direct electrolysis ideally requires a purified water system, such as a deionized water system or a reverse osmosis system. Thus, the disclosed system can include elements to purify any water being fed to the electrolyzers. In some embodiments, water can be deionized at each location where an electrolyzer is installed. In some embodiments, a centralized deionized water system can be installed, and deionized water fed through dedicated piping to the various rooms or points in the facility where the electrolyzer is employed to generate the ozone. As a result, the ozonated water can be ensured to be at the correct concentration, since the concentration of ozone in an ozonated water line will decrease over time, at the point of use.

In some embodiments, the system can include one or more ozone analyzers provided and mounted in a convenient location, such as close to or on the sink or near the toilet or on a wall or on the ceiling, etc. The analyzer continuously monitors the ozone concentration in the gas above the sink or wherever the analyzer is located in the room or environment. In some embodiments, the ozone analyzer sounds an alarm (e.g., a visual, auditory, electronic, etc. notification) that indicates when the level of ozone is above the desired or specified level. The ozone analyzer(s) output can be fed into the ozone control system, including a feedback control loop capable of controlling the concentration and/or flow of ozone gas output from the ozone generator and ozone flow control system, including shutting down the ozone generator altogether, until such a time as the ozone levels in air as analyzed by the ozone analyzers are below the desired level. If the ozone concentration in the air at the analyzer location(s) is too high, the controller may turn down the ozone gas addition rate or concentration of ozone in the gas being combined with water to make ozonated water.

The presently disclosed subject matter also includes systems and methods for removing ozone from the air. Fans or blowers can be installed that continuously or periodically mix the air in the sink basin with the surrounding air in the room. Sensors can be employed to activate if a person approaches the sink. In response, fans can be configured to draw the air out of the room through a vent, passing it first through activated carbon to absorb the ozone or through substances known to catalyze the destruction of ozone (e.g., Carulite 200, a granular substance made by Carus chemical company that catalyzes the destruction of ozone), or passing the gas through a chamber in which the gas is exposed to 240-315 nm UV radiation, which will destroy ozone, or combinations of these methods, before discharging the air into a room or vent.

It is known that 240-315 nm UV radiation will destroy ozone. If no persons are present and it is desired to reduce the concentration of ozone in the air above the sink, radiation of these wavelengths can be emitted in the sink area. These wavelengths are advantageous in that they are also germicidal and will help disinfect the air into and surfaces onto which they are emitted.

For applications where persons are not present for extended periods of time (such as in a restaurant or office building or store at night) disinfection cycles using the ozone can be more intense, with higher concentrations or higher flow rates or longer application times, or combinations thereof, being used. In such situations, if the more intense disinfection cycle is timed for earlier in the unoccupied period, significantly more ozone may be fed to the piping and emitted into the area. Since ozone decays over time and converts back to oxygen spontaneously, the rates of ozone feed to the room, plumbing fixtures, or drain system can be controlled such that by the time people reenter the area, the concentrations are again below the maximum allowable levels in air. Such administrative controls may even be used in facilities that are continuously occupied, provided that no one is allowed to enter the room or bathroom while the more intense disinfecting cycle is being performed. This may be accomplished by a janitor performing a more intense disinfection cycle after ensuring no one is in the bathroom and putting up barricades in front of the bathroom door. Alternatively, a nurse can perform a more intense disinfection cycle of the sink, etc. in the bathroom adjacent to a patient's room while the patient is asleep or sedated.

The disclosed system and method provide for a user interface on the ozone system to manually select the higher intensity disinfection cycle. The control system may give the operator a set time (such as 5-10 minutes) after activating the cycle to close the doors and exit the room. A system is provided to indicate (for example using a light or audible message or alarm) when the more intense disinfection cycle is taking place. In some embodiments, the system provides door contacts and motion detectors that are input into the ozone control system. When the door is closed and no motion is detected, the ozone feed to the drain piping may start or increase. If the door is opened, the ozone feed may shut off or decrease.

In some embodiments ozone can be incorporated into water using standard techniques, typically using a venturi tube through which water is pumped to create a low-pressure area into which ozonated air or oxygen is drawn and mixed into the water. The water for creating ozonated water can be taken from the water supply lines feeding the area or feeding the plumbing fixture. Ozone can be incorporated into cold water since colder water can hold more dissolved gas than warmer water. In some embodiments, a "tee" is provided in a water supply line feeding a plumbing fixture such as a sink or toilet, and water is fed to the ozone generating system for ozone incorporation using standard techniques. The ozonated water can then be fed to the plumbing fixtures and used in a manner previously described, such as pumping the ozonated water through a set of spray nozzles mounted in a toilet bowl or on a sink or sink faucet or in a shower area to spray ozonated water on the faucets and sink or shower surfaces, and the like.

Ozonated water may also be sprayed anywhere in the shower or tub to disinfect the surfaces and drains. In some embodiments where water-proof walls and/or floors are provided and a floor drain is provided, when no one is in the room, spray nozzles spraying ozonated water on the walls and/or floors periodically may be performed. For example, in a hospital, nursing home, restaurant, hotel, office building, gymnasium locker room, or swimming pool shower area, etc., a nurse, janitor, housekeeper, night shift worker, or other attendant can clear debris from the bathroom or shower area floor, set the ozonated water control system for a disinfection cycle with say a five minute delay for them to exit the room. Ozonated water can then be generated by the system and method described above, and disinfecting water can be sprayed onto the tiled walls and/or floor and/or plumbing fixtures in a bathroom for a nightly or periodic disinfection. The ozonated water spray can be left on for an extended period of time, even an hour or more, for better, more thorough disinfection than what would be achieved by manual cleaning of the surfaces. Since the ozone will be generated inexpensively from air and electricity, such a periodic cleaning will be safe, more effective, less labor intensive, and less expensive overall compared to manual cleaning of the bathroom or other areas with plumbing fixtures.

To this end, the system and method provide a user interface that allows the user to set the times at which the ozonated water spraying will commence, for how long the spraying will continue, and other parameters necessary for automated disinfection when persons are not in the immediate vicinity of where the disinfection is taking place. In some embodiments, the ozonated water spray control system can be equipped with motion detectors or other person detecting sensors that communicate with the control system and turn off the control system when persons are detected in the vicinity of the spray system. In other embodiments, a door position sensor may be provided to prevent the spray system from turning on if a door is opened. In some embodiments, both a door position sensor and a person detection sensor are provided with inputs into the control system so that the system may be turned off or not turned on if a person is present or a door is opened. In some embodiments, an ozone detector or detectors capable of determining the concentration of ozone in air are provided in communication with the ozonated water spray control system such that if the concentration of ozone in the air in the area exceeds a specified level, the control system can take action to decrease the amount of ozone in the area, which may be accomplished by turning off or turning down the ozonated water spray rate or by reducing the concentration of ozone in the water. One of the best ways of decreasing ozone concentration in actual testing was found to be the application of a fan to facilitate mixing, dilution of ozone in the air, and movement of the ozone to other areas. Any combinations of the person detection sensor, door position sensor, and ozone concentration sensor are also envisioned for input into the ozonated water spray controller or fan.

It has been discovered in testing of the invention that when ozonated water is pumped to and sprayed out of a nozzle that creates a fine spray, ozone dissolved in the water will escape from the water into the air, thus depleting the water of ozone before it can contact the surface, thus resulting in noticeably less disinfection, and in some cases a marked visible increase in mold growth from spraying surfaces with water with insufficient ozone content. Therefore, it is desirable when using ozonated water to disinfect plumbing fixtures and surfaces to gently allow the ozonate water to exit the piping supplying the ozonated water and fall onto surfaces, through a larger opening and not through a spray nozzle that generates fine droplets. In general, applying large droplets or streams of ozonated water to a surface will result in better disinfection. In some embodiments, ozonated water is allowed to dribble or run out of holes in a supply pipe onto surfaces. In other embodiments, a gentle rotation of a stream of ozonated water may be provided that applies streams and large droplets of ozonated water onto surfaces.

In some embodiments, the disclosed system and method includes replacing a plumbing fixture faucet with a new faucet. In such replacement or new faucet installations, channels for the disinfecting fluids and wiring can be more discretely located or built into the faucet or more tastefully designed so as to not detract from the appearance of the faucet or other part of the plumbing fixture. The new sink faucet can include a line that rises up above the faucet and handles and sink basin capable of spraying disinfecting fluid down onto the faucet and handles and sink basin, with the spray falling predominantly into the sink basin for further sink basin and sink drain disinfection. The disinfecting fluid can be supplied by an ozone gas generating system installed under the sink, such as in a cabinet and out of sight. The system can be configured to draw water from the cold water line and incorporate ozone into the water line, then feeding the ozonated water to the disinfecting fluid spray line. Some of this ozonated water can optionally be fed to the cold water supply line coming out of the faucet itself or any other desired location in or around the faucet and faucet handles and/or may optionally be fed to the sink drain piping. Some of the ozonated water can be fed to a nearby toilet or nearby shower, if present, to spray the plumbing fixtures with ozonated water using a series of nozzles as described previously.

An ozone analyzer, if desired, may be mounted on the line used for spraying ozonated water onto the faucet and sink but mounted above the spray nozzle to prevent it from getting wet. A motion detector may also be provided along with this ozone analyzer to turn off or turn down the ozone generation when motion is detected, indicating persons are present. A new faucet and drain system with some or all of the above features could be installed on a sink by a professional in less than an hour, assuming wiring for power is available. A backsplash may be provided behind the faucet fixture, either built into the faucet or as a stand-alone backsplash that may be held in place by the base of the faucet.

In some embodiments, a system is provided to feed ozonated water directly into the sink drain line using standard techniques, such as providing a piping "Tee" in the trap or drain line or providing a pipe nipple on the drain line or trap into which the line feeding ozonated water can be attached. The disclosed system allows for the direct disinfection of the sink drain lines, where the colonization of pathogens may be greater than in the sink and on the faucet fixture, and on a more frequent basis or with more ozonated water than what is fed to the sink directly in embodiments described elsewhere. In these embodiments, ozonated water can be fed to the sink drain even when persons are present in the bathroom.

Adding ozonated water directly to the drain line of a sink (including spraying the ozonated water into the drain line near the top of the drain line near the bottom of the sink basin) can be used in conjunction with other embodiments mentioned herein. For example, the method and system can be combined with spraying the ozonated water onto the faucet from above the faucet. In some embodiments, the disclosed system and methods can be used as a standalone system and the only system and method for controlling pathogens in a sink drain system without installing the embodiments to add ozonated water into the sink basin and onto the sink faucets, etc.

In some embodiments, ozone gas or air comprising ozone can be added to the sink drain line directly, and in some embodiments the ozone gas can be introduced into the standing water in the sink drain trap. Beneficially, the system and method reduce the cost of disinfection and in some cases improve the effectiveness of the disinfection, as a system designed to generate and deliver ozone gas will generally be less expensive than a system that generates ozone gas and incorporates that gas into water to form ozonated water. Ozonated gas may be generated with an ozone generator known in the art, such as those that use corona discharge to generate ozone, with the ozone gas being emitted directly into the drain. If too much gaseous ozone is emitted into the drain, the ozone gas may push out of the drain or out of the drain overflow and into the area above the sink. This may result in offensive ozone smell or too high of a concentration of ozone in the air above the sink, and an ozone analyzer or monitor or sensor may be employed, as described earlier, mounted above the sink, communicating ozone readings wirelessly or through a wire back to the ozone system control module, One common feature found in kitchen sink faucets is a water spray hose integrated into the main faucet discharge or provided as a separate hose apart from the main faucet. The water spray hose can be used in the cleaning of the sink, to rinse dishes, to rinse fruit and vegetables, etc. In some embodiments, ozonated water can be fed to the hose, allowing the user to rinse the sink or any other objects manually with ozonated water from the hose. In some embodiments, an ozonated water supply hose can be provided under the sink for use in cleaning or rinsing objects, including the manual washing of the sink basin, filling wash buckets on the floor, spraying onto a floor or floor drain, spraying onto or into a nearby plumbing fixture such as a toilet or shower, or any other use. Supplying ozonated water through a hose useful to facilitate periodic manual cleaning of the sink or other object may facilitate a less expensive system than other embodiments described herein in which ozonated water is sprayed into the sink automatically. Optionally coupling a manual periodic cleaning of the sink basin with an automated system to regularly inject ozonated water into the drain line, the combination can be sufficient to keep most pathogens under control.

One or more of the disclosed embodiments can use chemicals other than ozonated air or ozonated water as disinfectants. For example, hydrogen peroxide at any concentration (e.g., 2-10% in water) can be stored in a container under the sink and pumped to the various spray nozzles mounted on or in the faucet or in the drain line as previously described for embodiments using ozonated water. In some embodiments, water from the cold or hot water supply lines can be mixed with the disinfecting chemicals to dilute them prior to pumping the diluted disinfecting chemicals into the spray nozzles or faucet or drain, etc. A concentration of hydrogen peroxide or other chemical to be applied to a plumbing fixture for the purposes of disinfection may be for example 0.01% by weight, or 0.1%, or 1%, or higher or lower values. These values are given as examples and are not meant to limit the invention. In some applications, more frequent application of a more dilute disinfecting solution may be desired, whereas in others, a more concentrated disinfecting may be used but may be used less frequently due to cost. Dilution may be essential to cost effectively utilize chemicals that have to be purchased and loaded into a storage container. One way to accomplish the dilution is to take water from the hot or cold water supply line and send it through a venturi device, with the disinfecting chemical being pumped or gravity fed into the low pressure neck of the venturi device. The water and disinfecting chemical are mixed and transferred to another storage tank or directly to the spray nozzles or openings at the plumbing fixture. Beneficially, more concentrated chemicals can be stored in the feed container, thereby minimizing the number of times the feed container needs to be refilled and minimizing the handling of the chemicals. The advantages of using liquid disinfectants other than ozonated water is that significant savings in equipment costs and power consumption may be realized compared to ozone generating systems.

In some embodiments of the present systems and methods for disinfecting sinks and other plumbing fixtures, a single system for generating ozonate water can be installed. The disclosed system supplies ozonated water to multiple sinks and/or plumbing fixtures, each equipped with spray nozzles or openings or other embodiments. In such systems, the ozonated water control system can be designed to supply ozonated water to the spray nozzles, openings, drains, faucets, etc. of a first sink for a specified amount of time, and then the supply can be automatically diverted by automated valving well known in the art from a first sink to a second sink for a specified amount of time, then to a third sink or toilet or other plumbing fixture, etc. The sinks and plumbing fixtures may be in the same room, such as a public bathroom with multiple sinks and toilets, or the sinks may be in different rooms with the ozonated water or ozonated gas being pumped from one room to the next through piping. In this way, the initial cost of the ozonated water supply system can be spread out over multiple plumbing fixtures.

Ozone analyzers or sensors may be used to help manage the ozone in the air near the plumbing fixtures in which ozone gas or OW are being used as disinfectants. The ozone analyzer may sound an alarm, may provide a visual indication such as a red light or flashing light, may send a signal to a control console such as a nurse's station, or other indication that the air near the plumbing fixture comprising ozone above a certain preset alarm or action level. The preset alarm level may be set at the level of maximum concentration for continuous breathing in an 8 hour day, the maximum 8 hour exposure level currently set at or around 0.1 ppm. Alternatively, the alarm level may be set lower or higher than the cited level. The alarm level can be an indication for persons to leave the area and/or for an operator to take an action (such as to turn off the ozonated water or ozone gas addition system). In some embodiments, the output of the ozone analyzer can be fed back to the OWS system and/or ozone gas generating system to turn down at least one of: the ozone concentration, flow rate of ozonated water or ozonated gas being fed to the plumbing fixtures, including turning off the flow or increasing the time between ozonated water or gas treatment cycles.

In some embodiments, a fan or other air circulating device can be provided (e.g., near the plumbing fixture). The fan or circulating device can be positioned above the sink and/or mounted on the faucet fixture and pointed at the sink basin to circulate the air near the plumbing fixture and mix it with air further away from the plumbing fixture. In this way, ozone that may accumulate in a higher concentration near the plumbing fixture where ozonated water is being used for cleaning, for example, is diluted throughout the bathroom. As a result, the ozone concentration near the plumbing fixture is less likely to exceed the established limits, thereby enabling more ozonated water or ozonated gas to be fed to the fixture and therefore more disinfecting to be accomplished before the ozone analyzer detects a level of ozone in the air that exceeds the set amount. In addition, the level of ozone in the air throughout the bathroom and/or environment increases slightly, thereby enabling more disinfecting ozone to penetrate the nooks and crannies of more places throughout the room or environment, and thus achieving higher levels of disinfection in the environment surrounding the plumbing fixture.

In some embodiments, systems and methods are provided to reduce the amount of ozone in air to help keep persons entering the room or bathroom or environment safe and/or to reduce the amount of offensive ozone odors in the air. Ozone removal may be accomplished by providing vents, fans, and/or other air exchanging devices known in the art for removing the air from the environment. Ozone destruction may be accomplished by the application of UV or ultraviolet radiation (e.g., UVC radiation in the 240 nm to 280 nm range, which is known to break down ozone). The present system and method provide for the use of UV emitting device (such as a low-pressure mercury vapor lamp) to break down ozone in the air.

UVC radiation may also be used in addition to or apart from the purpose of destroying ozone to further enhance the disinfection of the surfaces in the room where the plumbing fixture disinfection system is installed, as UVC radiation is also known to destroy microorganisms. For example, one or more UV lamps can be mounted in an environment (e.g., bathroom), such as on the ceiling and spread out to cover the majority of the room with UV radiation. As the air laden with ozone travels in an upward direction from a sink drain or toilet into which ozonated water is being sprayed, the UV radiation beaming down from the ceiling helps destroy the ozone in the air. As a result, offensive odors and the chances of overexposing a person to ozone gas are minimized.

Further, UVC radiation also has disinfecting properties, and will kill microorganisms. Because UVC may be harmful to the eyes and skin of persons, UVC radiation can be best employed when persons are not present in the bathroom. To this end, a door position sensor and/or person detection sensor may be provided. The sensors detect whether the door to a room (e.g., a bathroom) is open or closed and whether a person is in the room. The sensors can feed information to the ozone and UVC lamp control systems. In some embodiments, if the door is open, no ozonated water can be fed to plumbing fixtures, and the UVC lamps are kept off. If the door is closed, the person detection sensors, such as motion detectors, can determine if there is a person in the room with the door closed. If a person is detected, the ozonated water and UVC lamps are still kept off. If the door is closed and no person or movement is detected after a certain period of time (e.g., several minutes), the ozonated water can be turned on and fed to the plumbing fixtures, and the UVC lamps mounted on the ceiling initiated.

The disclosed arrangement has the benefit of maximizing disinfection when persons are not in the room by simultaneously using ozonated water in the plumbing fixtures and UVC disinfecting other places in the environment. In addition, the readiness of the room in the event that a person suddenly enters the room is maximized by keeping the ozone in the air at lower levels. In some embodiments, if a person were to open the door to the room, the door position sensor can send a signal to a control system that shuts off both the UV lamps and ozonated water supply system until the person leaves, and the cycle can be started over again. In some embodiments, the UV lamps can be left off or in a lower output state until the ozone analyzer detects levels in the environment above a certain amount, at which point the UV output is increased by turning on UV emitters or by increasing the output of emitters by means known in the art. In some embodiments, ozone in the air can be controlled and reduced by circulating the air in the room through a solid medium capable of destroying ozone, such as through a bed or container or filter that includes manganese dioxide or copper oxide catalyst, although any catalyst or materials can be used. In such embodiments, air may be drawn from near a plumbing fixture that is being disinfected with ozonated water or ozonated gas and passed through a filter or cartridge comprising an ozone-destroying catalyst and then discharged into the room or into a vent.

Testing of the present invention revealed that if soap scum or other residues are not removed, the ATP results are not as good. This may be due to bacteria lodging in soap scum or other deposits. Another reason is that water does not always wet soap scum easily, and thus disinfecting chemicals may bead up and not contact the surface to disinfect it as well. Regular removal of soap scum, by means known in the art such as manually scrubbing a plumbing fixture or using chemicals formulated to remove scale and soap scum, may be necessary and desirable along with the use of the present system and method for automated disinfection of plumbing fixtures to achieve the best possible disinfection results.

The present system and method provide for liquid disinfecting chemicals to be fed into a toilet bowl continuously or intermittently through tubing or piping. The source of the liquid disinfecting chemicals may be a storage container or a distributed piping system or structure, as described elsewhere, and the chemicals may be fed by pumping, air pressure, gravity flow, or other means known in the art. The rate of flow of disinfecting chemical may be controlled by means known in the art for controlling the flow of fluid, such as manual or automated control valves, restricting orifices, and the like. Some embodiments employ a simple tube that sits on top of the toilet bowl rim but under the seat and discharges fluid into the bowl, pointed downward into the water and in some embodiments the tube opening is located under the static water level in the toilet bowl so that the chemicals are discharged directly into the water in the toilet bowl. In some embodiments, the tubing is made of stiff material, such as stainless steel, that holds its shape and is shaped to hug the inner surfaces of the toilet bowl to minimize obtrusiveness of the tubing. The disinfecting fluid in this embodiment can be ozonated water or ozonated gas; ozonated gas is discharged below the surface of the water in the bowl so as to get more of the ozone to dissolve in the water to disinfect the water and lower parts of the bowl.

The present invention provides for a system and method of disinfecting a toilet bowl by providing at least one and a multiplicity of spray nozzles or openings from which disinfecting fluid is discharged into the toilet bowl above the water level, this multiplicity of spray nozzles or openings is configured into a ring mounted near the top of the toilet bowl with spray nozzle discharges oriented so as to spray disinfecting chemicals onto surfaces of the inside of the bowl, including the underside of the upper rim of the toilet bowl, the disinfecting fluid is ozonated water, and the disinfecting fluid tubing is made of stainless steel, the disinfecting tubing is mounted under or mostly under the upper rim of the toilet bowl so as to be as inobtrusive as possible and to allow the spray nozzles to better disinfect under the upper rim of the toilet bowl. Brackets that hold the disinfecting chemical tubing in place onto the toilet bowl or onto the toilet seat may be provided. This configuration is only one of many that are envisioned and is not meant to limit the invention in any way, as any number of nozzles on any number of tubes arranged in any convenient arrangement are included in the scope of this invention.

In some embodiments of the present invention a toilet seat is provided that provides a more complete seal to the top of the toilet bowl rim to include disinfecting fluids in the toilet bowl. Many toilet seats have just a few relatively small feet that touch the toilet bowl rim, and the weight of the person sitting on the toilet seat is transferred to the toilet bowl rim through these relatively small feet. The feet are small so as to minimize contact with the toilet bowl rim, thereby minimizing surfaces to clean. In the present invention, the toilet seat contacts the top of the toilet bowl rim in many more places, making contact in at least 50% or at least 70% or at least 80% or at least 90% of the circumference of the rim. Contact of the seat with the toilet bowl rim may be made with hard material capable of transferring the weight of the user to the toilet bowl rim, or the weight of the user may be borne by several small feet as is currently done and other non-weight-bearing material may be used to create contact with the toilet rim, such as plastic or foam or wood or other material. The purpose of making contact with the surface of the toilet bowl rim is to create a seal so that disinfecting liquids and gases emitted for the disinfecting of the bowl do not readily escape into bathroom or onto the outside of the toilet bowl. This high-contact toilet seat allows more thorough disinfecting of the toilet bowl. In some embodiments, the high-contact toilet seat comprises a full oval or other shape around the entire upper rim of the toilet bowl rim and does not include the horseshoe-like gap in the forward part of the seat like many toilet seats do; this feature likewise helps contain disinfecting chemicals in the toilet bowl. In some embodiments, this high-contact toilet seat is semi-permanently mounted onto the toilet bowl rim using clamps or other removable attachment mechanisms such that the toilet seat is not able to be readily raised by the user but is firmly attached to the toilet seat rim. In other embodiments, vapors are less of a problem than liquids escaping the area between the toilet seat and upper surface of the toilet bowl, and in these embodiments it may be desirable to mount a weir on top of the toilet bowl rim. This weir may simply be a bead of caulk run around the outer edge of the upper surface of the top of the toilet bowl rim, or the weir may be made of a more rigid material and mounted onto the top of the toilet bowl. The top of the weir may touch the bottom of the toilet seat. The primary purpose of the weir is to keep disinfecting liquids spraying or dispensed into the bowl to disinfect the bowl from leaking out of the toilet bowl between the seat and the toilet bowl.

Similar to many available toilet seat designs, toilet seat lids are intentionally designed to minimize contact with the toilet seat, probably for sanitary reasons, and to this end they may feature two small feet on the bottom of the lid that support the weight of the lid on the toilet seat when it is closed. The result in many toilet seat lids is a gap between the toilet seat and the toilet seat lid that exists in almost the entire circumference of the toilet seat lid. With the intention of the present invention to disinfect the toilet bowl with gaseous and liquid chemicals, this gap will result in chemicals being emitted outside the bowl, which may waste chemicals or render them less effective, may create a mess outside the bowl, or even emit hazardous chemicals into the air at unacceptable levels. In some embodiments of the present invention, a toilet seat lid is provided that closes this gap between the toilet seat and the toilet seat lid when the toilet seat lid is in a down position. Closing this gap needn't be a tight seal and needn't block all of the gap, but in some embodiments the gap between the toilet seat and toilet seat lid can be closed at least 50%, or at least 60%, or at least 70%, or at least 80%, or at least 90% when the toilet seat lid is in a down position on the toilet seat. This gap may be closed by providing material to fill the gap, such as plastic or an elastomeric material or wood or any other convenient material, chosen from materials that are resistant to the chemicals being used to disinfect the toilet. In one embodiment, a ring of soft foam, such as strip insulation used for window weather-proofing, with a cross section of a rectangle or circle or other shape is attached to the bottom of the toilet seat lid around the circumference of the lid and located at such a point so that upon closing the lid, the foam is in contact with the upper surface of the toilet seat and fills at least 90% of the gap between the toilet seat and toilet seat lid when closed. Caulk may also be used to fill this gap, such as silicone caulk applied to the seat or cover or to the upper rim of the toilet bowl itself. In actual testing, latex caulk broke down after only several days of ozonated water application, whereas silicone caulk held up for more than months of operation.

Chemicals other than ozone gas or ozonated water can be added to the toilet employing some of these systems and methods. For example, hydrogen peroxide solution may be pumped through spray nozzles to disinfect the toilet bowl or toilet seat. The chemicals may be pumped from a chemical storage container or from a piping system running through or near the room through which the disinfecting chemicals are pumped.

The systems and methods noted above are particularly suitable for a so-called western style toilet or a toilet where a person sits on a toilet seat mounted on or above a toilet. Eastern style toilets frequently do not have seats, and users squat over the toilet which comprises a hole in the floor through which waste passes. These types of toilets are disinfected in the present invention by providing a means to emit disinfecting chemicals into or onto the toilet, for example through a tube that discharged disinfecting chemicals above or below the water level of the water in the toilet, if any. Disinfecting chemicals may be sprayed onto the toilet in a manner so as to wash the toilet, disinfect the toilet surfaces, and collect the majority of the disinfecting chemicals into the toilet for disposal. In one embodiment, a ring of disinfecting spray nozzles are arranged around the perimeter of the toilet, with nozzles capable of emitting disinfecting chemicals in a manner to clean the toilet surfaces and push debris and liquid toward the toilet low point or drain. A person detector may be provided so that if persons are in the vicinity, no disinfecting chemical is emitted, whereas if no person is detected, chemical spray is emitted. In this embodiment, ozonated water is particularly suitable, since ozonated water does not pose a safety hazard to a person's skin or lungs as may ozone gas or other chemicals. Thus, residues of ozonated water on the toilet when a user approaches would not constitute a safety concern. The ozonated water may also be provided in some embodiments to the users using the toilet for cleaning themselves after using the toilet, thus further helping to limit the spread of pathogens.

Urinals. Urinals may similarly be disinfected by applying a disinfecting liquid to the surfaces, using a plurality of spray nozzles to simultaneously clean and disinfect the inside and in some cases the outside surfaces of the urinal.

Rooms or portions of rooms that are waterproof and have floor drains may also be disinfected by the present system and method. A restaurant bathroom for example may be disinfected by ozonated water spray (or other disinfecting fluids may be used instead of ozonated water) that is being generated in a unit located under the sink. Water proof tiles line the walls and ceiling, and a floor drain is provided to collect the ozonated water. The system may be preset for a time of day to commence the disinfecting cycle, or an operator may clear the room and then activate the ozonated water disinfecting cycle by any number of means known in the art, such as a button or a button with a timer giving the operator a certain amount of time to exit the room, remote control from an operator outside the room activating or controlling the disinfection cycle, etc. In some methods, an operator may first check the room for debris and removes loose debris (e.g. toilet paper, paper towels, trash, etc.) or sweeps the room; an operator may even perform some cleaning of the sink, toilet, etc. to remove debris that cannot be removed with the disinfecting chemicals. After the operator has exited the room, a disinfecting cycle commences in which disinfecting fluid is sprayed on the plumbing fixtures, walls, and floor of a room, with the excess disinfecting fluid draining into a floor drain. Of course, toilet paper or paper towel dispensers would need to be shielded from water spray by providing a waterproof enclosure or removing them prior to cleaning. The disinfection spray may be out of all spray nozzles at the same time, or to minimize the size and cost of the ozonated water supply unit, the spray nozzles may be cycled, with one or a first set of the spray nozzles discharging for a specified amount of time, say five or ten minutes, then turning off, then a second or second set of spray nozzles discharging ozonated water onto the walls, etc. for a second specified amount of time, and so on until all the areas that are desired to be disinfected are sprayed. The cycle optionally may be then repeated. Any desired arrangement and number of discharge openings or spray nozzles is contemplated in this invention. The cycle may be commenced during times of infrequent use, such as at night, after which there would be time for the water to dissipate or dry and any ozone that has diffused into the air to dissipate. An ozone analyzer may be provided for the air to either feedback to the ozonated water supply control circuitry for optional control of the amount of ozonated water emitted into the room (e.g. reducing the amount of ozonated water emitted into the room if the ozone in the air reaches a certain level) or warning persons who might be preparing to enter the room (e.g. with a warning light or indication inside or external to the room being disinfected) or both.

The room disinfection system described above may also be suitable for locker room showers associated with gymnasiums, pools, school locker rooms, sports team locker rooms, etc., in which multiple shower heads, showering stations, walls, and floor are desired to be disinfected when no persons are present. An ozone analyzer may be provided in the vicinity, such as on the ceiling, and if the ozone levels in the air exceed a certain level, the ozone in the water can be adjusted downward or eliminated altogether until such a time as ozone levels no longer exceed a desired level. Any room or environment may be disinfected in like manner, when a means of removing excess disinfecting fluid is provided, such as a floor drain. Other rooms or environments where this system and method may be useful may be in a food processing plant or food preparation area, where for example stainless steel equipment or tables are used for processing food and are periodically washed with ozonated water according to the present invention.

The systems and methods previously described for dispensing disinfecting chemicals onto plumbing fixtures such as faucets, faucet handles, sinks, sink basins, sink drains, walls and floors, etc. may also be useful in other plumbing fixtures, for example, a bathtub, a shower stall, a bathtub and shower combination, or a shower room. Tubing supplying a disinfecting chemical may be supplied to a spray nozzle or nozzles or other means for discharging the disinfecting chemicals onto a shower head or onto a shower water supply control valves or fixtures or onto shower or bathtub walls or onto a floor of a bathtub or shower area, etc. In the case of for example a shower room with multiple shower heads in one room or area or a shower stall, a plurality of disinfecting chemical nozzles or holes or openings in the piping may be provided arranged in a manner to apply disinfecting chemicals, for example ozonated water, on the majority of the shower stall or shower room walls, floor, water control handles, shower heads, soap holders, even ceiling areas provided care is taken to not spray lighting or electrical fixtures with disinfecting fluids if they are not designed for such service. In short, many surfaces in a shower area or in a bathtub, including walls around a bathtub, may be treated with disinfecting chemicals according to the present invention. In the case of bathtubs, where there is a wall on one or two or three sides of the bathtub, spray nozzles may be provided mounted on the bathtub itself to spray all the sides of the tub and floor of the tub, and where there are walls adjacent to the tub, spray nozzles may be provided higher up on the wall and pointed primarily downward onto the wall, if desired, to disinfect the walls around the tub, the disinfecting chemicals of course running down into the tub and down the tub drain.

Since the discharge drain piping in bathtubs and showers is usually not as readily accessible as for example a sink drain, the present system and method provide for adding disinfecting chemicals to the drain directly, by running tubing carrying disinfecting fluid to a point just above the drain or even down into the drain to disinfect the drain line. In one embodiment disinfecting tubing lines and spray nozzles are provided to spray disinfecting fluid on the inner surfaces of the bathtub, the bathtub faucet and associated valves, handles, etc., and down into the drain itself. In this embodiment, since closing the drain plug would not be possible with tubing being run into the drain, a modified drain plug is also provided with a notch where the tubing is located so that the drain plug may close. Since tubing run across a floor can create a tripping hazard in a shower area, the tubing may be shrouded in a cover strip designed to minimize the tripping hazard, as is known in the art for example for power cords run across a floor. In one example, the disinfecting tubing is run into the drain and ends with a nozzle that emits disinfecting chemical below the drain cover.

In some embodiments, ozonated water is generated in a bathroom and used to disinfect a sink, or a toilet, or a shower per the disclosures previously made. In addition, UV radiation emitters or a plurality of UV radiation emitters are arranged in the bathroom at various locations, mounted on the ceiling or on a support structure above the heads of persons in the bathroom. A door position sensor is provided, along with a person detection system in the bathroom. When the door is closed and no person is detected in the bathroom, the UV radiation emitters emit UV radiation into the room, and the disinfecting chemical addition system is activated, ozonated water, to emit disinfecting chemicals to the sink, etc. The UV radiation also helps destroy airborne ozone, thus helping to keep the concentration of ozone in the room low. At least one ozone concentration analyzer is provided mounted at some location(s) around the room. If the ozone concentration exceeds a desired level, the ozone generating system may turn down or shut down the ozone or ozonated water being used to disinfect the plumbing fixtures. Thus, by means of monitoring the ozone concentration in the air in the room and using that to control the amount of ozone being emitted into the room, plus the use of UV radiation that has the double benefit of destroying pathogens and destroying excess ozone in the air, by these means the amount of ozone in the air can be controlled, and persons can be kept safer when entering the room. If someone such as a patient opens the door to use the bathroom, for example, the door position sensor indicating an open position sends a signal to the ozone and UV radiation control system to shut down the UV radiation and optionally also the ozonated water system. Once the person finishes using the bathroom and closes the door behind them, the disinfection cycle is repeated. An indicator such as a red or green light may also be provided outside the door of the bathroom to indicate whether the bathroom is safe to enter. For example, if the ozone in the air exceeds a desired level, and the system is working as described to reduce the level of ozone in the air, the indicator light may show red until the ozone in the air is below the desired level. Alternatively, a respirator may be provided to patients or other persons to don prior to entering the room if the levels are above the desired level.

One of the primary disadvantages of using ozonated water in the disinfection of sinks or other plumbing fixtures is that some ozone will disengage from the water and will enter the air above the water. Whereas ozone in water on the skin or even ingested into the body does not present a safety hazard, breathing air comprising ozone at concentrations above the established limits (typically 0.1 ppm for an eight-hour exposure) may present a safety hazard. Even if the concentrations in air do not exceed the eight-hour exposure limit, the smell of ozone may be unpleasant and undesirable for some. In addition, persons in a health care setting, where this invention is envisioned to be useful, may be particularly sensitive to ozone inhalation and may require a maximum ozone limit set lower than the typical 0.1 ppm limit.

The present invention provides for a means to lower the amount of odor emitted from the system. In the case of sinks, the present invention provides for spraying disinfecting fluid, in some embodiments ozonated water, intermittently or continuously onto the faucet and sink basin for disinfecting the faucet and sink basin and subsequently the drain as the fluid drains from the sink basin into the drain. Also as previously described, the present invention provides for directly discharging disinfecting fluid, ozonated water, continuously or intermittently into the inside of the drain piping on the discharge of the sink basin, just below sink drain plug or just below the point where the fluid leaves the sink basin and enters the drain piping. It is expected that either of these disinfecting fluid application locations, above the sink basin or directly into the sink drain, may be effective for achieving acceptable levels of pathogen reduction. In still other embodiments of the invention, both spraying disinfecting fluid onto the faucet or sink basin and spraying disinfecting fluid directly into the sink drain may be employed either simultaneously or at different times.

In one embodiment, to minimize the odor emanating from the ozone escaping into the air, only the emission of ozonated water into the drain piping is used. Since the fluid is being emitted into the drain piping, there is significantly less opportunity for ozone disengagement from water and escape into the air above the sink basin compared to emitting the ozonated water as a spray above the sink basin. This embodiment may be used in situations for example where it is determined that periodic manual cleaning of the sink basin and faucet by normal cleaning means coupled with spraying disinfecting ozonated water into the drain piping is sufficient to control the pathogens of concern. In similar embodiments, ozonated water is injected into the sink or plumbing fixture drain line and ozonated water is provided on the supply side of a faucet, and in some variations of this embodiment the user can select between ozonated water coming from the faucet or non-ozonated water. In this embodiment, the pathogens are controlled in the drain line piping while some disinfecting is also accomplished on the sink basin and faucet when the user turns on the water. Indeed, these embodiments may be advantageous from a cost standpoint since it will avoid the expense of providing disinfecting spray onto the faucet and sink basin and associated hardware such as an optional backsplash. In cases where spraying ozonated water into a drain line still produces too much unwanted ozone in the air above the sink, in some embodiments an automated drain plug control mechanism may be provided to close the drain plug when ozonated water is being emitted into the drain line, thereby reducing still further the amount of ozone that may escape into the air above the sink.

The present system and method also provide additional ways in which unwanted ozone in the air may be reduced. In some embodiments, the air above the sink comprising higher concentrations of ozone is circulated and mixed with air in the room that comprises lower concentrations of ozone. This circulation is accomplished by any means known in the art for circulating air, done using a fan or blower. In other embodiments, the air above the sink is drawn into a conduit or piping or tube using means known in the art for creating a sufficient vacuum such as a fan or blower or vacuum pump, etc. to draw air into the conduit. Once in the conduit, the air comprising ozone may be passed through a bed of manganese or copper oxide or other substance known in the art to destroy ozone back to oxygen. Alternatively, the air containing ozone may be passed through a bed comprising carbon particles such as activated carbon or particles comprising carbon such as wood particles, the ozone thereby reacting with the carbon to form carbon dioxide, thus reducing the amount of ozone in the air. In one embodiment, the air intake, fan, and ozone destroying bed are all mounted on, behind, or near a backsplash. An ozone sensor or analyzer may also be provided near the ozone destroying unit, the output of which may be used in various ways, such as to turn on the ozone destroying unit if the ozone levels are found to be above a predetermined amount. The ozone sensor may also be used to turn down or off the ozone spray or ozone emitted into the sink drain.

In other embodiments, once in the conduit the air comprising ozone may be exposed to ultraviolet radiation using wavelengths effective for breaking ozone ($O_3$) down into oxygen molecules ($O_2$), the purpose of exposing the vapors to radiation in a conduit being to shield persons in the environment from being exposed to the harmful ultraviolet radiation. In other embodiments, the conduit is vented to another area where the ozone is not objectionable, for example outdoors. In other embodiments, the air comprising ozone is discharged into drain piping, including into the water housed in traps or downstream of traps in the sewer piping or into another plumbing fixture such as a toilet bowl. In still other embodiments, ultraviolet radiation in the 240-320 nm range is emitted into the air above the sink, in some embodiments the radiation emitters are located on a ceiling or wall above a sink area. In such embodiments, the intensity of the ultraviolet emitters may be controlled by providing a person location detector sensor and optionally a door position sensor and control circuitry known in the art that will turn off or turn down the ultraviolet radiation being emitted when a person enters the area or room or optionally when a door to a room is open or combinations of a door being open or a person being detected in the vicinity of the radiation emitters. In still other embodiments aimed at reducing the amount of ozone in the air, deodorizing substances may be emitted into the air which are common in the art of air deodorizing. One example of this embodiment is the use of an electric air freshener, a common household plug-in air freshener, an example of which is a Glade® Plugins® scented oil made by SC Johnson and Son, Inc. designed to plug in to a wall socket electrical receptacle and emit aromatic fragrances into a room and advertised to provide one month of air freshening with one refill pack. Aerosol sprays are also used for air freshening and may be incorporated into the present invention. These and other air freshening technologies are known in the art and are included in this aspect of the invention. Such organic chemicals may reduce the offensiveness of ozone or other disinfecting chemicals in the air by one or more of two mechanisms: first, offensive ozone odors are masked by pleasant smelling organic compounds, and second, the organic compounds may provide an airborne substance with which the ozone may react and thereby be destroyed. Air which may include ozone is drawn through a bed of an ozone-destroying catalyst such as manganese oxide by a fan, after which on the discharge side of a fan a scented oil or mist or other air-freshening organic compounds are emitted into the air leaving the fan by evaporation or mist generation or other means known in the art for freshening air. Any combinations of any of these features for reducing the amount of unwanted ozone in the air above a sink or plumbing fixture are also within the scope of this invention.

The present invention provides for cleaning the outside of toilets by providing disinfecting fluid distribution system such that at least one disinfecting fluid outlet, a spray nozzle, is configured in a way so as to spray disinfecting fluid on a least a portion of the outside of a toilet. In some embodiments, a plurality of spray nozzles are provided and so arranged so as to apply disinfecting fluid to the outside of a toilet from one or more positions or angles or heights or combinations thereof so as to cover as large of a percentage of the outside area of a toilet as possible. In some embodiments, spray nozzles are provided mounted on or in a toilet seat lid such that disinfecting fluid may be applied or sprayed onto the outside of a toilet surface, optionally including onto the outer surfaces of a toilet seat and optionally onto the outer or upper surfaces of a toilet seat lid. In other embodiments, the disinfection of the outside of a toilet may be accomplished by providing disinfecting fluid spray nozzles and associated fluid supply lines mounted on a wall or floor or ceiling or on a toilet.

The present invention provides for supplying disinfecting fluid to a bidet, a common device to wash or spray the private parts (crotch, anus, labia, etc.) of a person immediately after defecating or urinating or using the toilet, for the purposes of washing and disinfecting the skin of said person. The present invention provides for using the disinfecting fluid as the primary feed to the bidet, meaning the disinfecting fluid will be sprayed directly onto the skin of a person using the toilet, and the disinfecting fluid coming into contact with a user's private parts. Therefore, using disinfecting fluids which are effective for disinfection and also safe for human skin and private part contact are necessary. In some embodiments, the disinfecting fluid in the present invention can be ozonated water, with dissolved ozone levels of up to 0.1 parts per million by weight (ppm) ozone in water, or up to 0.5 ppm ozone in water, or up to 1 ppm ozone in water, or up to 2 ppm ozone in water, or up to 5 ppm ozone in water, or up to 7 ppm ozone in water, or up to 10 ppm ozone in water, or more than 10 ppm ozone in water. These ozone concentrations in water apply to all embodiments of the invention in the present application.

Bidets come in many varieties and are manufactured and sold by a number of different companies, in the USA by WebGerms Health Inc. (aka Alpha Bidet), TotoUSA, Inc., Tushy, Inc., and other manufacturers. Any bidet style or type is included in the present invention. Typically, the water feed to a bidet, which is used to wash the private parts of a user, is taken directly from the cold-water feed line upstream of and feeding the toilet flush system, in some toilets the toilet tank. In some bidets, the water feed to the bidet may be temperature controlled by taking water from both a hot water supply line and a cold-water supply line and mixing the hot and cold water to the user's desired temperature in the bidet control system prior to discharging the water onto a user's private parts. In the present invention, ozonated water may be fed into either or both the hot water supply line to the bidet or the cold-water supply line, since ozone will decompose more rapidly at elevated temperatures and since cold water can hold more dissolved ozone gas than can hot water. In some embodiments, spray nozzles are also provided to spray the bidet system with disinfecting fluid to disinfect the bidet, particularly the parts of the bidet that extend into or over the toilet bowl or which may be more easily contaminated with contamination and pathogens. In some embodiments, the bidet is manufactured in a manner known in the art so as to be able to be sprayed on the outside with disinfecting fluid, such as ozonated water, to disinfect the bidet and bidet control panel, which is touched by users and which may also become contaminated with pathogens.

The present invention provides for a system and method to supply disinfecting fluid to a multiplicity of plumbing fixtures, including plumbing fixtures in different rooms and including a multiplicity of plumbing fixtures within a same room. The means of distribution in this embodiment is through a disinfecting fluid header. A disinfecting fluid header may carry disinfecting fluid into a room where one or more take-off tee connections allow disinfecting fluid to be conducted to a plumbing fixture such as a sink or a toilet. One line take-off line from the header may feed one plumbing fixture or may be further split to serve multiple user needs, as is common in the art of fluid distribution. The header may be made of any suitable material for housing the disinfecting fluid such as stainless steel or PVC piping or tubing. In some embodiments, the disinfecting fluid circulated through the header is ozonated water, in which case the benefit of circulating the fluid through a header is to allow the ozonated water to be optionally circulated to an ozone generator or ozonated water generating system such that the concentration of ozone in the water may be refreshed and maintained, since ozone spontaneously decomposes over time back into oxygen. For this reason, circulating the ozonated water through a header with take-off points close to the point of use allows the benefits of economy of scale and cost reduction of installing larger ozonated water generation equipment capable of supplying ozonated water to multiple plumbing fixtures located at various points or rooms in a building while at the same time ensuring the quality or sufficient concentration of ozone in the water when it is required at the plumbing fixture.

In another embodiment, electrolytic devices known in the art and commercially available for generating ozone directly in water are provided near the pluming fixture or point of use. However, current electrolytic ozone generating devices benefit from being fed a higher quality or more pure water, such as water from a deionized water system or from a reverse osmosis water purification system. If typical tap water is used in such devices, the lifetime of certain components in the electrolytic cell may be shortened and thus necessitate more frequent replacement. Providing a header feeding a purified water supply to a multiplicity of electrotroylzers located closer to the points of use may have the advantage of ensuring high quality ozonated water on demand when the user requires while eliminating the need for a large ozone generating system that circulates ozonated water through a header, ozonated water which may not be used and which is continuously decomposing and in need of refreshment.

Since reverse osmosis systems and other water purification systems are becoming much more common and less expensive, it is becoming ever more economically feasible to provide an RO or other water purification system feeding an electrolytic ozone-generating cell which produces ozonated water. This combination of water purification plus electrolytic ozone generation in a combined package could then be used to service one or more plumbing fixtures. For example, an RO system designed to supply a household kitchen sink could be used in a hospital or nursing home bathroom to supply purified water to an electrolytic cell generating ozone and making ozonated water. This ozonated water could then be fed to a sink or toilet or shower or plumbing fixture of the present invention. This combination of equipment is expected to be much smaller and compact and less expensive that current ozonated water generating systems which typically first purify air, then generate ozone in the purified air using corona discharge methods, then force that ozonated air into water in a venturi tube and mix tank. Generating ozonated water electrolytically from purified water and using that ozonated water to disinfect plumbing fixtures according to the present invention is expected to become a lower cost method of practicing the present invention.

The present system and method provides for data related to the automated disinfecting systems described in this application to be collected and transmitted to a computer system designed to collect and store the data and optionally communicate the data to users, for monitoring the status of the system. The computer system may be located in the disinfection system control module, such as the control system for generating ozonated water and dispensing the water onto or into plumbing fixtures or plumbing fixture water feed or drain piping, or the computer system may be located in a place remote to the disinfecting system. For example, in healthcare settings, disinfecting systems may be installed in a multiplicity of bathrooms in a particular area such as the bathrooms associated with patients' rooms in an ICU (intensive care unit). Data related to the operating of the disinfecting systems may be transmitted wirelessly or through hardwiring to a centralized computer system at a nurse's station or other location in the hospital or even outside the hospital building itself. A system for collecting and monitoring the data may be provided as a stand-alone computer optionally with a display and user interface, or the system for collecting and monitoring the data may be provided as a program or an app designed to be run on a PC or workstation or server or other computer device known in the art for storing and running programs and storing data from electronic systems.

Data related to the operation of the plumbing fixture disinfecting system may be electronic data obtained from the Plumbing Fixture Disinfection System (PFDS) control module, such as whether or not the control system is on, whether or not the system is generating ozone in the case of ozone-generating PFDS, critical operating parameters such as ozone concentration, or disinfecting solution active ingredient concentration, flow rates, whether or not and at what times the system is dispensing fluid into the plumbing fixture and at which places, in the case where disinfecting fluid is dispensed into a plumbing fixture at multiple points, the flow rate or time of fluid dispensing, the oxidation reduction potential of the disinfecting fluid, the temperature of the fluid or the room, the pressure of the water feed or disinfecting fluid in a line, whether or not there is a person in the room, whether or not ultraviolet emitters are emitting ultraviolet radiation, whether or not the door to the bathroom is open or closed and at what times it is open or closed, the concentration of ozone in the air in the bathroom, and other desired information. The determination of this data is provided by means known in the art for measuring and transmitting such information electronically, such as an ozone or disinfecting agent concentration analyzer or a pressure sensor with electronic transmitter, and the like. Electronic sensors of this nature are very common in the art and usually convert measurements into electrical signals that are transmitted by wiring or wirelessly to a system which stores the data. These electronic measurements may be transmitted to a computer system, wirelessly for example over a hospital's Bluetooth system, for monitoring and storage. A data monitoring system may serve the function of recording the disinfection cycles and system parameters for quality control or for research and development purposes. A data collection and monitoring system may also enable remote monitoring of the system. For example, a contractor may be responsible for maintaining the operation and safety of ozonated water disinfection systems of the present invention located in bathrooms throughout a hospital. Being able to monitor the operation of each system remotely may greatly reduce the manpower needed to ensure disinfection quality and greatly reduce the need for manual monitoring and the corresponding disturbances to patients and healthcare workers that would result. The same type of system may be useful in a hotel setting, where PFDS are provided in a room, for example a bathroom, and more in a multiplicity of rooms. Data on the operation of the PFDS are collected and monitored in a location on the hotel premises or even remotely to the hotel premises, said system communicating to or alarming a person monitoring a PFDS that something is not working as intended and action should be taken. The person may then notify a person on the premises that action should be taken, or they may take action themselves to rectify the situation. In some embodiments of the present invention, a feedback system is provided that enables commands to be sent from the centralized monitoring station to a PFDS, such as a command to turn on or off the PFDS or an adjustment to the PFDS control parameters, such as the number or duration of disinfection fluid emissions onto or into a plumbing fixture in a 24 hour period, or any other control system input.

One application envisioned for the embodiments of the present invention is in healthcare settings, specifically hospital settings or nursing home settings, and more particularly in hospital and nursing home settings that have incalcitrant infectious diseases in sinks, toilets, showers, and other plumbing fixtures that routine or normal cleaning methods are unable to adequately control. For embodiments of the present invention that utilize ozonated water generation systems, such as the AOS, OST, or OXS series of products made by Oxidation Technologies, LLC located in Inwood, IA, these commercially available ozone generation units are small enough to be located in a corner of a room or a closet, etc. The smallest of these, the smaller of the AOS product line, may be small enough to be located under a sink or in a cabinet under or near a sink. The AOS line of products only need a water feed line, a cold-water line, and normal 120 VAC single phase power such as is available in buildings and homes throughout the USA accessible by plugging a simple standard electrical wall plug into a wall socket. In some embodiments, an ozonated water system is fed by a cold-water line closer to the water inlet into a building or area of a building, with ozonated water being distributed through the cold water distribution system downstream of the ozonated water system, with the cold water distribution system or header feeding parts of a building, such as a hospital ward or floor, or a smaller building such as a restaurant or even a private home.

In other embodiments it is desirable to mount an ozonated water or disinfecting fluid system on a wall or even on a ceiling to move it out of the way yet keep it close to the point of use, in which cases the units may be mounted into wall studs using hardware and other means known in the art. In situations where mounting the ozonated water or disinfecting fluid system onto a wall or ceiling is not possible or not desirable, the present invention provides for a frame made of metal or plastic or wood or other suitable material to be mounted onto the walls or ceiling or as a free-standing structure mounted against a wall or walls and supported at least in part by the floor. For example, metal rods approximately ½" in diameter, square or round, may be placed vertically in the four corners of a small bathroom, such as against the wall. Horizontal rods may be mounted near the ceiling attaching to these vertical rods using screws or brackets or other hardware known in the art to connect metal rods together, thus creating a self-supporting metal frame capable of supporting the required weight and onto which the ozonated water or other PFDS, Plumbing Fixture Disinfection System, may be attached. In this manner, disinfecting fluid generation systems may be located in space-constrained areas. An advantage of a frame structure for mounting the PFDS is that power, device, and sensor wiring as well as water and disinfecting fluid supply lines may also be mounted on the frame without having to drill holes in the walls, etc., for mounting such necessary components. It will be recognized that additional supports and struts may be mounted on the frame in any desired orientation and configuration for the purposes of increasing the strength or stability of the frame or providing convenient locations for mounting components of the disinfection system. In some embodiments, one or more UV disinfecting lamps emitting disinfecting ultraviolet radiation at wavelengths sufficient to destroy pathogens, such as in the range of 240 nm to 320 nm, are provided in a room or environment in addition to one or more PFDS. In these embodiments, the one or more UV emitters may be mounted on the support frame in some locations for the destruction of pathogens, such as near a ceiling or a wall. The one or more UV emitters may be arranged over one or more plumbing fixtures, such as a toilet or a sink or both. Mounting the UV emitters on the frame may be desirable for several reasons, such as to avoid damaging a ceiling which would result for example from making holes in the ceiling for mounting hardware, to enable the mounting of the UV emitters in locations where it would not be possible to mount the emitters if they were to be supported by the ceiling due to mechanical or weight constraints or the location of other objects on the ceiling that would prevent the mounting of the emitters on the ceilings, such as vents, ducts, fire suppression sprinkler systems, and the like.

One established technology from which the mounting system may be borrowed is in the building of shelving. Shelving may consist of stand alone or wall mounted units. Any such means known in the art for building shelving or mounting shelving on a wall or other part of a building may be employed for the purpose of mounting a disinfection system of the present invention.

In some embodiments of the present invention, a plumbing fixture disinfecting system is provided, an ozonated water-generating system, capable of feeding ozonated water to one or more plumbing fixtures in a bathroom, for example a sink, a toilet, and a shower for the emitting of disinfection fluid onto a plumbing fixture or into a faucet or shower head or water line feeding a plumbing fixture. In addition, in this embodiment, one or more UV emitters are provided to supplement the disinfection capabilities of the disinfecting fluid. At least one person detection sensor is provided to determine whether or not there is a person in the room, and a door position sensor is provided to detect whether or not a door into the room is open or closed. Upon determining that a door leading into the room is closed, the system will determine, using input from a person detection sensor, whether or not there is a person in the room. If there is not a person in the room and the door is closed, the control system provided by the present invention for controlling the disinfection system may turn on the UV emitters and may emit UV radiation into the room to disinfect surfaces onto which the radiation falls, either directly or secondarily after reflection off of a first surface. The control system provided by the present invention may also emit disinfecting fluid onto or into a plumbing fixture or piping leading to or from a plumbing fixture for disinfecting the plumbing fixtures and preventing the recontamination of the plumbing fixture by pathogens. In this manner, by the use of both disinfecting fluid applied directly onto or in a plumbing fixture as well as radiation emitted so as to fall on surfaces that may not be exposed to disinfecting fluid, such as a wall or floor, much more of the bathroom surfaces and fixtures may be disinfected than either the disinfecting system or UV emitters alone may be able to achieve.

The benefits of automatically and repeatedly throughout a day disinfecting multiple surfaces and fixtures by the multiple methods of UV and disinfecting fluid emissions, as described in the previous embodiment, are several, first, that disinfection of more surfaces and more areas where recalcitrant pathogens persist than would be possible with UV emitting devices or disinfecting fluid system alone. Second, the repeated cross-contamination of pathogens from one location to another will be reduced, for example, with no UV radiation to disinfect a floor or walls, persons entering a bathroom may become contaminated with pathogens and transfer pathogens to for example a bathtub or a shower or other place in the bathroom. Similarly, the use of UV radiation without plumbing fixture disinfection may allow repeated transfer of pathogens from for example a toilet or a sink onto persons or other surfaces in the bathroom, including aerosols that are known to be generated from the flushing of toilets. Third, the transfer of pathogens from the bathroom to other rooms in the building by persons entering the bathroom will be similarly reduced.

In yet another embodiment, a plurality of interconnected disinfection systems described in the previous embodiment are provided such that one or more components of the plurality of interconnected disinfection systems is shared between the plurality of interconnected disinfection systems. For example, in a hospital ICU ward, a disinfection system of the previous embodiment is provided in which an ozonated water system is provided to disinfect a sink, a toilet, and a shower in a patient's room's attached bathroom. UV emitters may also be provided in this bathroom as part of the disinfecting system as previously described. In an adjacent patient's room's bathroom, a similar arrangement is provided for emitting ozonated water into plumbing fixtures and UV emitters, however, it is found that it is not necessary to install an ozonated water generation system in the second bathroom because there is excess capacity from the system in the first bathroom to supply ozonated water to the second bathroom, thus saving money. An ozonated supply line may be run, in some embodiments using the shortest path possible, possibly by running the ozonated water supply line along with associated control wiring directly through a wall to an adjacent bathroom. In this embodiment, in the second bathroom it will be necessary to provide spray nozzles for dispensing ozonated water onto a sink, a toilet, a shower, or onto the desired plumbing fixtures, but these may be fed from the ozonated water generator located in a first bathroom. To minimize situations in which ozonated water is demanded in both bathrooms simultaneously, thus resulting in lower water flows or the need to install a larger ozonated water generation system, the control systems for each bathroom may be in communication so that the periodic ozonated water spray to each plumbing fixture does not occur simultaneously. In other embodiments, one control system is provided for both bathrooms, with the system coordinating ozonated water emissions alternatively to each plumbing fixture of the combined bathrooms' plumbing fixtures. UV emissions in each bathroom would be controlled as separate rooms, since UV emissions are based on whether or not a person is in the room, whereas ozonated water may be emitted into a plumbing fixture while a person is in a room.

Another feature of the present invention related to this is the thorough application of disinfecting fluids to the areas of a plumbing fixture that may not normally be wetted or contacted with disinfecting fluid. For example, application of disinfecting fluids to the faucets and sink basins as described in this invention will be more effective in disinfecting the plumbing fixture than just running disinfecting fluid through the faucet and letting it run down the drain or than cleaning the plumbing fixture manually with disinfecting fluids.

After a person uses a plumbing fixture, such as a sink, a toilet, or a shower, in some embodiments, a person detection sensor in communicates with the disinfection system that a person has entered the proximity of the plumbing fixture and has left the proximity of the plumbing fixture. At this point the disinfection system sprays disinfecting fluid into or onto the plumbing fixture to disinfect the plumbing fixture. The system may continue with the previous disinfection cycle timing in use prior to the user using the fixture or the system may reset the disinfection cycles after use.

For shower disinfection systems, a disinfecting fluid support rod may be provided, similar to a shower curtain rod which may attach to a wall at each end, onto which disinfecting fluid tubing and nozzles are mounted. In some embodiments, the rod itself also serves as tubing for disinfection fluid such as a stainless steel tube with nozzles along the side located at various spacings such as ever 6 or 12 inches. The rod may be mounted in parallel with and about the same height as a shower curtain rod with the spray nozzles pointed mostly inward and arranged so as to spray and wet the majority of the area of the shower stall sides, including the shower or tub floor and the shower curtain if desired. If a shower has a door instead of a shower curtain, the rod may be installed at any convenient location or height being supported by means known in the art for supporting a shower rod or other device on the wall of a shower. Multiple disinfecting rods may be used in a single shower. Disinfecting fluid is supplied through piping or tubing to the disinfecting fluid tubing mounted on the disinfecting fluid support rod and turned or off by the disinfecting fluid control system.

The present system and method provide for disinfecting a plumbing fixture and providing disinfecting fluid from a faucet or shower head or other fluid dispensing device for disinfecting objects such as hands, wounds, utensils, tools, medical equipment, medical supplies, and other objects. The present system and method provide for disinfecting a plumbing fixture, the disinfecting fluid in these embodiments being ozonated water with an ozone concentration of less than 40 ppm, or an ozone concentration of less than 30 ppm, or an ozone concentration of less than 20 ppm, or an ozone concentration of less than 10 ppm.

In various installations of the present invention, the flow of disinfecting fluids to and through nozzles and other openings may be affected by the distance of the lines, bends in the line, different faucet designs, different spray system designs required to accommodate different faucets, different sizes of plumbing fixtures requiring differing flows of disinfecting fluid, and other differences between the installations. In such situations it may be necessary to increase a line size to decrease pressure drop, or install an orifice or restriction to increase pressure drop, or employ a control valve in the line to control flow, or many other means known in the art for achieving a desired flow rate through a piping system, and all such means are incorporated into the present invention as needed to achieve the purposes of delivering a desired amount of flow of disinfecting fluid to a plumbing fixture.

Different nozzle spray patterns may be employed in the present invention to control or guide the direction of the disinfecting fluid. Likewise, guides may be installed made of metal or plastic or other suitable material to guide and shape the direction of the spray or shield certain areas of the plumbing fixture from being sprayed with disinfecting fluid if so desired.

Disinfecting spray systems may also be provided for applying disinfecting fluid to the outside of plumbing fixtures, such as to the outside of a sink or a toilet or a bathtub, for the purpose of disinfecting the outside of the fixture so as to prevent the spread of pathogens that may be on the outside surfaces of plumbing fixtures. With such application of disinfecting fluid to the outside of a plumbing fixture the disinfecting fluid may not conveniently enter a drain of the plumbing fixture or into a floor drain. The problem of course in disinfecting the outside surfaces of a toilet with disinfecting fluid, for example, are that puddles of fluid may accumulate on the floor and produce a tripping hazard or may cause water damage. In embodiments where the disinfection of the outer surfaces of a toilet or plumbing fixture are desired, moisture absorbing mats may be placed on the plumbing fixture or on the floor near the plumbing fixture or below the point of disinfecting fluid emissions, for example on the floor underneath and around the outside of a toilet. Such absorbing pads are known in the art, such as commercially available pads or mats placed underneath urinals to absorb urine and water splashing from a urinal or similar units around toilets to collect and absorb urine or water or other substances. For example, such absorbing pads for toilets and urinals are the Spartan® Urigard® C (for commodes) or Urigard® U (for urinals) Disposable Deodorizing Mats made by Spartan Chemical Company. The present invention may incorporate such fluid absorbing devices to facilitate the disinfection of the outside of plumbing fixtures without creating a mess or tripping hazard on the floor near the plumbing fixture.

The present system and method provide for the installation of a monitor or output screen or light or some other means of communicating the status of the bathroom to persons inside or outside the bathroom or room in which disinfecting fluids are being automatically emitted. For example, in the case of the use of ozonated water being used to disinfect plumbing fixtures in a bathroom attached to a patient's room in an ICU, a display screen or indicator lights may be provided near the outside of the door that indicate whether or not the system is dispensing disinfecting fluid and optionally what part of the dispensing cycle it is in. If an ozone analyzer is also provided for the air space in the bathroom, a display or indicator lights may also indicate what the ozone concentration (or other disinfecting chemical) is in the air and whether or not it is safe to be in or to enter the bathroom. If UV irradiation is also being performed in the bathroom, an indicator outside or inside the bathroom may tell persons whether or not UV is being emitted. The present system and method also provide for person detection sensors, such as a motion detector, located outside the bathroom or room in which disinfection fluids are being automatically dispensed, said sensors being in communication with the fluid dispensing control system. If a person is detected outside the bathroom near or approaching the bathroom door, the control system may be programmed to then shut down or turn down or suspend the fluid dispensing cycle or the UV emissions or both. Ozone or other active ingredient detectors may also be located outside the room being disinfected with disinfecting solution dispensing optionally with alarms or other means to alarm patients or personnel if the ozone or other active ingredients are escaping from the room in which they are being emitted and entering surrounding rooms or areas. These ozone or active ingredient detectors (or sensors or analyzers) may also communicate the reading electronically back to the fluid dispensing control system for data storage or transmission, or in other embodiments, the system may decrease or turn off fluid dispensing based on readings of high concentrations of active ingredients in surrounding rooms. The present system and method provide for continuous automated monitoring of active disinfecting chemicals or ingredients using sensors or detectors or analyzers placed at various points in the rooms, particularly the monitoring of active ingredients in the air, such as ozone concentrations in the air in the room or in surrounding rooms or areas near where the disinfecting fluid is being dispensed, and the storage of these data readings, such data being needed to ensure that the system is working properly and the workers or other personnel in the areas are being kept safe.

UV emissions in an environment in which ozonated water is being emitted will also have the benefit of destroying ozone in the air if there exists a concern about the amount of ozone getting into the air when the ozonated water is being dispensed onto or into a plumbing fixture. The UV radiation, in the 240 nm to 320 nm range, will also destroy microorganisms, a further benefit of emitting the UV radiation. The present invention provides for a system and method for controlling the UV emissions such that UV radiation is not emitted during all or part of the time when the disinfecting fluids are being dispensed but UV radiation is emitted when the disinfecting fluids are not being emitted. This is accomplished by combining the control system for the UV emitters into the control system for the disinfecting fluid dispensation, effectively making one control system for both the disinfecting fluid dispensing and the UV emitters. The goal of turning off or decreasing the amount of UV emissions during times with disinfecting fluids are being dispensed can be accomplished by the control system by means known in the art for writing algorithms, computer programs, and controlling electronic circuits. The computer program controlling the UV emissions and fluid dispensing may simply call for turning off or to a lower level the UV emissions during times when disinfecting fluid is being dispensed and turning on or to a higher level the UV emissions during times when disinfecting fluid is not being dispensed.

The present system and method provide for an input device to allow users to input parameters such as the number of disinfection cycles in a 24 hour period, the time duration of disinfection dispensing events to each plumbing fixture and the wait time between each dispensing event, whether or not the system is turned on, a feature useful if a patient is admitted for example with extreme sensitivity to the disinfecting fluid, which plumbing fixtures or areas are to be disinfected, whether or not the UV turns on to enhance the disinfection, and any other parameters that may be built into the system as parameters that may be changed or varied in some way by the user. Such input devices may be a touch screen located on or near the dispensing equipment, such as a touch screen located on or near the disinfecting fluid storage container or disinfecting fluid generating system, or on or near a wall or doorway near the room where the dispensing events are taking place, such as on the wall in a bathroom near the doorway, or the input device may be a computer screen using a graphical user interface (GUI) or other input device located in a central location such as a nurses station, a room in another part of the building, or even in a remote location, or the input device may be a portable device such as a cell phone or a tablet in wireless communication with the disinfection system. The disinfection system may also be configured to be manually operated by inputting information into the input device. For example, in cases where an input screen controlling a disinfecting fluid dispensing system of the present invention is located near a doorway leading into a bathroom or on a wall inside the bathroom, the system may be set to be off until an operator such as a nurse manually inputs a command into the input device to start a disinfection cycle or even a single disinfection fluid dispensing event. This feature may be useful in cases where automatic cycling of disinfection fluid dispensing events is not desired, yet one or two events a day, to be initiated manually, is desired. The nurse, in this example, may find an opportune time in which the patient may not want to use the bathroom and input commands into the input device that a disinfecting cycle is to be performed, at which point the system may begin disinfecting a plumbing fixture or fixtures in the programmed sequence.

In some embodiments of the present invention, ozonated water is fed to a faucet, such as to a cold water line on a sink. An electronically-activated actuator is also provided which is capable of opening and closing the valve controlling the flow of the ozonated water into a sink, such as the cold water valve on a sink. The actuator may at pre-determined times open the ozonated water valve and allow ozonated water to flow into the sink for a pre-determined amount of time, then the actuator closes the valve. The actuator may be configured to not interfere with manual operation, therefore allowing a person to open the valve when the actuator is in a closed position, and allow a person to close the valve when the actuator is opening the valve. The cycles of opening and closing the valve may be controlled by an electronic control system which may also allow users to input the times and durations of automated opening and closing of a valve. Thus, a system and method are provided for automatically disinfecting a sink basin and sink drain piping by periodically opening and closing a faucet valve supplied with disinfecting fluid, thereby allowing disinfecting fluid to intermittently be discharged into the sink basin through a faucet. This system and method may be useful for achieving a certain degree of sink and plumbing fixture disinfection without the spray systems described elsewhere in this invention. Some degree of disinfection will be accomplished every time either a user opens a faucet to dispense disinfecting fluid or the system automatically opens the faucet valve and dispenses disinfecting fluid. This system may be useful to keep sinks disinfected that are equipped with ozonated water but are not used frequently or long enough for the sink and drain piping to receive adequate disinfection from daily use.

In some embodiments, it is desirable to add a surfactant or wetting agent or combinations thereof to the disinfecting fluid to help with wetting the surfaces onto which the disinfecting fluid is applied. The need for this is evident from the standpoint that different surfaces have different surface energies, and surfaces that have lower surface energies than water, such as surfaces made of Teflon® polytetrafluoroethylene or surfaces with a coating of grease or oil on them, will not be wetted well by aqueous-based cleaning agents which are the primary focus of the present invention. In such situations, water will bead up in certain areas and run off the surfaces more quickly than on higher surface energy surfaces. It is also common on plumbing fixtures for films and scum to form on the surfaces with use over time, including biofilm formation, any of which may form a surface on the fixture or object that alters the characteristics of the surface energy of the underlying substrate making it more difficult to thoroughly wet with disinfecting fluids. To combat this, it is common in the art to add surfactants or wetting agents, etc. to cleaning agents, for example, "surfactant" is listed as an ingredient on "Great Value Cleaner with Bleach" sold by Wal-Mart, along with "sodium hypochlorite, sodium hydroxide, and fragrance." "Wetting agent" is listed as an ingredient on SC Johnson Company's "Windex" brand cleaner, along with "water, carriers, cleaning agents, dye, and fragrance." Any wetting agent or surfactant or other agent known in the art for facilitating the effectiveness of cleaners and disinfecting agents when applied to surfaces are hereby incorporated as possible additives to the disinfecting fluids of the present invention, as are fragrances or dyes or other additives known in the art of cleaning and disinfecting fluid formulation.

The present system and method provide for the maintenance of a state of disinfection of plumbing fixtures or objects by the automated, periodic, no-touch application of disinfecting fluids to a plumbing fixture or object and optionally the addition of UV radiation in the room when persons are not present. The maintenance of a state of disinfection is hereby defined as the ability to check visibly clean surfaces onto which disinfecting fluid is applied according to the present invention for cleanliness at any time and find that the number of colony forming units, or CFU's, of a specified microorganism is less than a threshold number when a visibly clean surface is swabbed according to procedures standard in the art of testing surfaces for living microorganisms. A specified microorganism is any bacteria, fungi, or microorganism chosen by the user. Some microorganisms will be more difficult to disinfect than others, but it is an object of the present invention to provide a highly flexible system that will allow a user to easily change the disinfection fluid application parameters to allow more frequent or longer applications of disinfecting fluid, or to use in the same system stronger disinfecting fluids, for example to increase the strength of a hydrogen peroxide disinfecting fluid being used from 3% to 5%, to disinfect any microorganism to a desired level of disinfection. When CFU's are reported, they may be reported as CFU's per gram of sample collected or CFU's per ml of fluid sample or CFU's per cm2 of area swabbed or CFU's per swab that was submitted for testing. In the following CFU levels, any of these CFU units may be utilized, but in particular since it is a surface that is being disinfected, CFU's per cm2 or CFU's per swab will be in view when discussing the following limits, even though only the term "CFU" is used. The present system and method may maintain the average disinfection of a surface over at least two CFU tests such that that no CFU's are detected, typically denoted as "Not Detected" or "ND." The present system and invention may maintain the average disinfection of a surface taken over at least two CFU tests at less than 1 CFU's, or less than 2 CFU's, or less than 3 CFU's, or less than 5 CFU's, or less than 7 CFU's, or less than 10 CFU's, or less than 15 CFU's, or less than 25 CFU's, or less than 50 CFU's, or less than 75 CFU's, or less than 100 CFU's, or less than 200 CFU's, or less than 500 CFU's, or less than 1000 CFU's.

It is a further objective of the present invention to achieve the aforementioned maintenance of a state of disinfection of plumbing fixture or objects with minimal human or manual labor expended to clean the plumbing fixture, which may be needed from time to time to remove visible debris such as toothpaste in a bathroom sink or soap scum in a bathtub or fecal matter or dried urine in a toilet or scale from mineral or other deposits left from the impurities in the water or food and oil on the surfaces of a kitchen sink. Although the present system and invention will afford some disinfecting and some cleaning by virtue of the periodic application of disinfecting fluids onto a surface, and although the system may help reduce the time or number of manual cleanings required for these fixtures or objects, in general a periodic manual cleaning to remove visible debris or surface-energy altering films from surfaces onto which these disinfecting fluids are applied according to the present invention are expected to still be required. It is an object of the present invention to maintain a state of disinfection on a surface even though there may be visible debris or surface-energy altering films accumulating on the surface, however, that state of disinfection may involve maintaining a state of disinfection at a higher CFU count than would be possible if the surface were free from visible debris or surface-energy altering films. It may even be possible in some situations for the present system and method to maintain the same state of disinfection with visible debris or surface altering films present as would be achievable if the surface was visibly clean and free from surface altering films. In other words, the system and method of the present invention may keep even visibly dirty surfaces relatively free from specific pathogens.

The present system and method may maintain a state of disinfection of a plumbing fixture or object according to the following sequence. First the system of the present invention is installed to automatically and periodically apply disinfecting fluids to a plumbing fixture or object. The control module for the system is programmed or set up to dispense disinfecting fluids at a duration and frequency chosen by the user. Second, the surface to be treated with disinfecting fluids of the present invention is cleaned manually to remove all visible debris or surface-energy altering films. A swab of a surface may be taken and the initial level of CFU's present on a surface may be determined at this point. Third, the present system and method are activated, and disinfecting fluids are periodically applied to the surface or surfaces, at least once every 24 hours, at least once every 12 hours, at least once every 6 hours, at least once every 4 hours, at least once every 3 hours, at least once every 2 hours, at least once every hour, at least once every 30 minutes, and at least once every 15 minutes. Fourth, visible debris or surface-energy altering films that may accumulate on the surfaces to which disinfecting fluid are being applied are periodically removed by manual cleaning, whenever it is evident that such debris or films are present. Fifth, at any desired time, when no visible debris or surface-energy altering films are present, and more after multiple applications of disinfecting fluid to surfaces where no visible debris or films are present, the surfaces are swabbed and CFU counts are determined.

The present system and method provide for safely installing the present system in rooms or areas where deadly pathogens may be present. In these embodiments, manual disinfection of plumbing fixtures or objects is first performed to the extent possible, followed by the generous application of additional disinfecting chemicals. For example, portable ozonated water generating devices are available, for example "MOB Series" portable ozonated water generating unit made by Oxidation Technologies, LLC of Inwood, IA, which can be brought near the contaminated sink to be disinfected, and copious amounts of ozonated water may be sprayed onto the surfaces or plumbing fixtures onto which the present invention is to be mounted. The outsides of the drain piping, if disinfecting fluid is to also be mounted in the drain piping as described elsewhere in the present invention, may also be sprayed with ozonated water or other disinfecting chemicals.

In some embodiments of the present invention, it is desirable to ring the fluid piping with dispensing nozzles on a plumbing fixture such as around the rim of a sink basin or along the edges of a tub. To lower the obtrusiveness of the fluid piping, it may be embedded in a sheath, made of softer materials such as a rubber capable of withstanding the chemical attack of the disinfecting fluid. The sheath may resemble an anti-tripping sheath that wires are covered by when they are run across a floor. In this manner, the sides of the plumbing fixture may be adequately covered with disinfecting spray with minimal inconvenience to persons using the plumbing fixtures. The sheath also provides protection for the disinfection fluid tubing and nozzles. The sheath may be mounted to a plumbing fixture or object using means known in the art, such as glues, screws, double-sided adhesive strips, and other means of attaching things to plumbing fixtures or other objects.

The system and method of the present invention provide a secondary benefit to plumbing fixture operation and disinfection in that the disinfectants, particularly ozonated water, may attack and break down or decompose debris in the plumbing fixture or drains, such as hair or toothpaste or other matter that may accumulate and build up as a sludge on the walls of the fixture or piping. As the disinfectant attacks and breaks down this organic matter, it is more easily carried away by water in the fixture. This results in fewer surfaces and masses in which pathogens may establish biofilms and colonies and may result in less plugged drains of plumbing fixtures.

The present system and method provide for the disinfecting of plumbing fixtures using the periodic application of disinfecting fluids to plumbing fixtures or other objects such as door handles, floors, walls, equipment, and other parts of buildings. The system comprises a disinfecting fluid delivery system comprising, in some embodiments, equipment to generate ozone on-site or near the point of use and incorporate ozone into water, and in other embodiments, equipment to store disinfecting fluids which are made off-site or not near the point of use. The system further comprises a disinfection fluid delivery system which may comprise a pump, tubing or piping, valves which may be opened or closed to allow flow controlled flow of disinfecting fluids into or onto a plumbing fixture or other object, and openings to allow for the discharge of disinfecting fluids into or onto a plumbing fixture or other object, and with openings equipped with nozzles, deflecting surfaces, or other means of spreading the disinfecting fluid onto a larger area than the cross sectional area of the opening, for example a nozzle with an opening size of one square millimeter may, by means known in the art for spraying fluids, spread the disinfecting fluid onto a surface such as the inside surface of a sink or toilet the size of tens of square millimeters or larger.

In this embodiment, it is not desirable to continuously apply disinfecting fluids to the plumbing fixture or object due to the effectiveness of the disinfecting fluid in killing microorganisms when applied with the present invention. In this embodiment, it is desirable to conserve on disinfecting fluid or to allow the system to apply disinfecting fluid to additional plumbing fixtures or objects, such as in the case where a single ozonated water-generating unit is capable of supplying ozonated water to multiple plumbing fixtures or objects in a room or in multiple rooms or multiple bathrooms. In this embodiment, a system is provided for controlling the application time or application amount of disinfecting fluid applied to a single fixture or object in a given period of time, such application time or times in a 24 hour day being less than 24 hours in a day. A control system is provided comprising valves known in the art which are opened for a period of time and closed for a period of time. The present invention provides for a system and method for manual operation of the valves to apply disinfecting fluid for a specific period of time during a day. For example, the bathroom attached to a patient's room in a hospital may be equipped with an ozonated water generating unit and tubing for conducting the ozonated water to a sink, a bathtub, and a toilet in the bathroom, with nozzles provided and mounted on or in those three plumbing fixtures or a drain of a plumbing fixture. It may not be desirable for the ozonated water to be emitted all of the time or even on a periodic basis. But it may be determined for example that to adequately control pathogens in these plumbing fixtures, ten minutes of flow of ozonated water to the plumbing fixtures per 24 hour period is necessary. The present invention provides for a system and method for operating the disinfection fluid delivery system manually to apply disinfecting fluid for a desired period of time. The ozonated water generation system may be turned on, or it may be left on in a standby mode, and a valve or valves may be operated to allow disinfecting fluid to be dispensed to a plumbing fixture (PF) or object. The valve or valves may be operated manually by turning a handle, or the valve or valves may be operated by entering a command into the system's input station, such as a keyboard or touchscreen, at which point the system sends an electronic signal to an electronically activated actuator mounted on a valve to open the valve and then close the valve once the operator gives an input command to close a valve or after a pre-set period of time. In this manner, the operator may manually choose when disinfecting fluid is dispensed.

In some embodiments, the dispensing of disinfecting fluid is more automated. For example, it may be determined that for a specific pathogen of concern that a 5 minute application every hour of disinfecting fluid comprising, for example, 3% hydrogen peroxide in water or 5 ppm ozone in water will be adequate to kill microorganisms and prevent the substantial further growth of microorganisms on a surface onto which the disinfecting fluid is applied, thus effectively preventing that surface from becoming a vector from which the specific pathogen might spread to other surfaces or individuals. The present system provides for a programmable operating mode in which the application of disinfecting fluid automatically occurs for 5 minutes each dispensing cycle time, such as each hour. In some embodiments, the system provides a user input interface to input the duration of disinfecting fluid dispensing and electronically controlled actuators on valves to turn on or off or up or down the flow of disinfecting fluid. If the system is installed in a bathroom, for example, and disinfecting spray is to be applied five minutes every hour to a sink faucet and basin, a sink drain, a toilet, and a shower, with the disinfecting fluid storage or generating unit in standby, the system may automatically actuate an actuator and open a valve on the fluid line to a sink faucet and basin, thus allowing fluid to flow first to the sink faucet and basin for five minutes, after which the valve is closed. The system may then activate a different actuator and valve combination on a line feeding disinfecting fluid to a sink drain and allow fluid to flow into the sink drain for five minutes, and so on until each PF has had a five-minute application of disinfecting fluid, and this cycle is repeated every hour in this example. The dispensing cycle time may be ideally adjusted by an operator, or at the time of commissioning, to be every hour, which may be a default time, or every ninety minutes, or every two hours or other unit of time the user inputs into the system so that the user can program the system to apply fluid to a PF or object for a specified number of minutes within a specified period of time.

In still further embodiments, the duration of flow to each PF may be adjusted individually, for example, the system's input device allows the user to program a different time if desired for each PF, for example, five minutes of fluid dispensed every two hours to a sink faucet and basin, twenty minutes of fluid dispensed to a toilet every two hours, and fifteen minutes of fluid dispensed to a shower every two hours. Other combinations of dispensing time or numbers of dispensing events in a dispensing cycle controlled separately to each PF or object are also envisioned within the scope of this invention to accommodate the fact that various PF's or objects may need longer or shorter, more frequent or less frequent applications of disinfecting fluid. Another variation within the scope of this invention is to provide a system which may, in addition to on or off operation, apply an increased or decreased amount of flow to a PF or object by controlling the degree of opening of the control valve, as is common in the art of automated flow control systems. The system may be equipped with a person detection system such that if a person enters the vicinity of a PF or object being disinfected, the application of disinfecting fluid may be stopped or not started, with the system continuing with the disinfection cycle where it left off after the person leaves, resetting the disinfection sequence, or adding disinfection fluid dispensing events as a result of a person having used or been near a PF or object. For example, a person detector may be provided for a bathroom, and if a person enters, the disinfection fluid application is stopped. When the person leaves the bathroom, the cycle may then initiate an immediate disinfecting cycle to immediately apply disinfecting fluid to one or more plumbing fixtures or objects and then reset the disinfecting cycle times or resume the previous disinfecting cycle, or other responses to a person having been in the room.

In some embodiments, a single disinfecting fluid storage or generation system (e.g. an ozonated water generation unit) may supply disinfecting fluid to multiple rooms and multiple fixtures within multiple rooms. In such situations, the configuration of piping and valving may follow that described above for a single bathroom with multiple fixtures. For example, a single disinfecting fluid generation system may supply ozonated water or hydrogen peroxide solution to a sink basin, a sink drain, a toilet, and a shower in each of two bathrooms, with the disinfecting fluid being sent for example at the start of a 90 minute disinfecting cycle first to a sink in a first bathroom in which the disinfecting fluid generation system is located for five minutes, then to a sink drain in a first bathroom for five minutes, then to a toilet in a first bathroom for ten minutes, then to a shower in a first bathroom for 15 minutes, then to a sink in a second bathroom for seven minutes, then to a sink drain in a second bathroom for seven minutes, then to a toilet in a second bathroom for 12 minutes, then to a shower in a second bathroom for 17 minutes, and then the system is in standby not sending disinfecting fluid anywhere until the 90 minute total disinfecting cycle is completed, and then the cycle starts all over again. The reason for adding a few minutes to the dispensing times for the plumbing fixtures in bathrooms further away from the disinfection fluid generation system is also optional but in the case of ozonated water may be desirable due to the decay of ozone in the lines once the flow is shut off. Until fresh ozonated water disinfecting fluid displaces the depleted ozone disinfecting fluid in the pipes from the previous dispensing event, the ozonated water will not be at full strength when delivered to a plumbing fixture. Of course, these fluid dispensing times and cycle times are completely arbitrary and are not intended to limit the invention in any way. In some embodiments, instead of inputting a cycle time, a rest time between dispensing events or at one or more points in a dispensing sequence may be inputted, for example after each disinfecting fluid dispensing event the system waits for a period of time before starting another dispensing event, or after dispensing fluid sequentially to each plumbing fixture or object, the system pauses for a period of time before resuming the disinfecting sequence all over again. In still other embodiments, a fixture such as a toilet may require more frequent disinfections than other plumbing fixtures, and in such cases the system may be configured to, for example, dispense disinfecting fluid first to a toilet, then to a sink, then back to the toilet again, then to a shower, etc., in any order and any number of dispensing events and durations desired. Programming for any of these and other described fluid dispensing times or sequencing are easily accommodated by computer programming known in the art. Any combinations of these modes of setting the disinfection fluid dispensing times or sequences is also envisioned, as are the disinfection of multiple plumbing fixtures or objects in multiple rooms, including two, three, four, five, and even more than five rooms all controlled by one disinfection fluid dispensing control system.

The system can be sized to handle any desired flow rates and times for any number of locations for any desired cycle times. Even one application of disinfecting fluid for a few minutes in a plumbing fixture once per week is envisioned in the present invention, as is a continual feed of disinfecting fluid to a plumbing fixture. These situations are mentioned as examples to highlight the flexibility of the system to disinfect multiple plumbing fixtures in multiple rooms; the more fixtures that can be disinfected with a single disinfecting fluid storage or generating system, the lower the overall cost will be.

In such situations where multiple fixtures or objects are being disinfected by a single source of disinfecting fluid, the valving which controls the flow to each fixture may be located close to the electronic control system with tubing or lines going to each of the fixtures, including fixtures in other rooms. In these embodiments, there will be fluid lines going to each fixture from the vicinity of the control system. In other embodiments, it is more desirable to minimize the number of fluid flow lines, and therefore a single disinfecting fluid line or fewer disinfecting fluid lines may be used for example to transport fluid to a sink, then to a shower, then to a toilet, then to a second bathroom where it likewise transfers fluid to a sink, a toilet and a shower, and at each fixture, there is a take off line to conduct fluid to that particular fixture along with a valve that controls the flow to that particular fixture. The electronic control system is in communication with each of these valves by hard wires, including wiring to power the actuators, mounted on or near the tubing for convenience, or wirelessly; in either case wiring for powering the actuator will be required.

In cases where fixtures in multiple rooms are being disinfected with one control system, and in such situations where person detection sensors are provided in each room to communicate the presence of persons with the electronic control system, the present system and method provide for being able to control each room separately according to use. For example, if one bathroom is used less frequently, the disinfection cycles can usually proceed uninterrupted as programmed, and if a second bathroom connected to the same system is used often, and therefore the disinfection cycles are repeatedly delayed or interrupted, the system provided is capable by means known in the art of computer programming to adjust the disinfection cycles of the fixtures in each room according to a predetermined algorithm and disinfection priority to provide optimal disinfection for both bathrooms. For example, if in the previous example of the plumbing fixtures in two bathrooms are being disinfected in a 90 minute cycle, and provided both bathrooms are equipped with person detection sensors that communicate to the disinfection fluid dispensing control system wherein the programming suspends the dispensing of disinfection fluid to a particular bathroom if a person is detected in that bathroom, and for example the second bathroom is occupied, the system may provide for an algorithm that suspends all fluid dispensing until the second bathroom is unoccupied, at which point it resumes going through its dispensing cycle where it left off. Or, in other embodiments, the programming may wait a prescribed period of time, and if the second bathroom is still occupied, the automated dispensing of fluid in the first bathroom continues as programmed even if the second bathroom remains occupied. When the second bathroom becomes unoccupied, the program may for example interrupt the dispensing cycle of the first bathroom to dispense disinfecting fluid to the second bathroom, or the program may continue to cycle through its dispensing sequence and disinfect the second unoccupied bathroom in its normal sequence. These are examples of the many ways the present system may be programmed to respond to events than may interrupt disinfection cycles and are in no way meant to limit the ways the system may be programmed to dispense disinfecting fluids, such programming flexibility being well-known and practiced in the art of programming and fluid flow control.

Figure 1C:
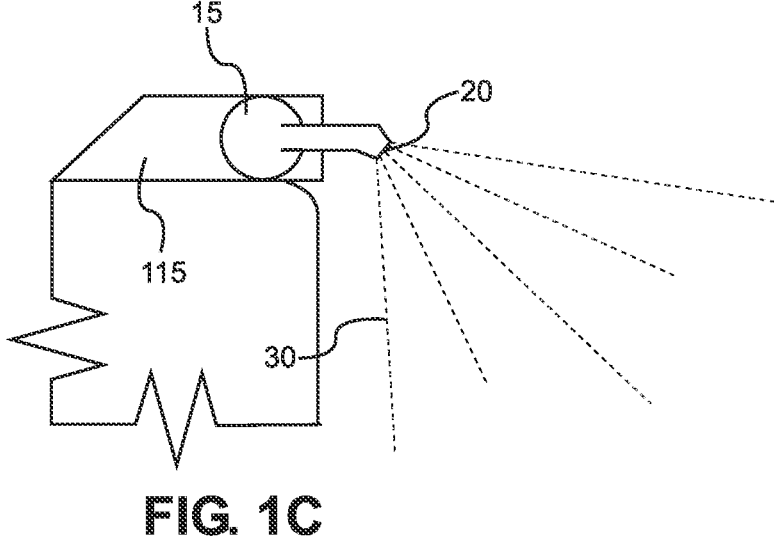
FIG. 1c is a front plan view of an encased fluid delivery header in accordance with some embodiments of the presently disclosed subject matter.

As shown in FIGS. 1a and 1b, to disinfect a sink basin 100 and associated faucet and faucet handles 110, an ozone system or other disinfecting fluid delivery system can be installed to deliver disinfecting fluid 30 through a disinfecting fluid header 5, which may split into an upper disinfecting fluid header for disinfecting the faucets and upper sink area 10, and an optional lower disinfecting fluid header for disinfecting the sink basin 15. In some embodiments, the disinfecting fluid delivery system can be installed on a cold-water line and located in a convenient location, for example under a sink or in a cabinet or closet. The disinfecting fluid headers in FIGS. 1a and 1b comprise spray nozzles 20 or other openings in the fluid header at convenient locations to distribute disinfecting fluid 30 on sink surfaces. In some embodiments, a backsplash 25 is provided that may support the disinfecting fluid header and help prevent disinfecting fluid from contacting the wall behind the faucet. In some embodiments, a germicidal radiation emitting device such as a UV lamp 40 shown in FIG. 1a only may also be installed, in this example on top of the backsplash, to provide additional disinfection. The addition of a UV irradiating device ideally also will be accompanied by a person detection system or sensor 60 in communication with control circuitry to turn off the radiation when a person is in the area. FIG. 1a also shows the optional addition of an air moving or air filtration system 50 also mounted on the backsplash that is capable of circulating the air over the sink area or moving air over the sink area through a filter or through for example a bed of granules of activated carbon or other substance capable of removing chemicals from air. FIG. 1c shows an option of encasing the fluid delivery header 15 in a soft or firm holding material 115 that may be comfortable to the touch of a user, protects and helps maintain the position of the header around the plumbing fixture, and is aesthetically pleasing. The system depicted in FIGS. 1a-1c can be modified for other plumbing fixtures such as tubs or showers, urinals, toilets, walls or floor areas that are designed to house water such as those areas of a building draining to a floor drain, and other plumbing fixtures.

Figure 2A:
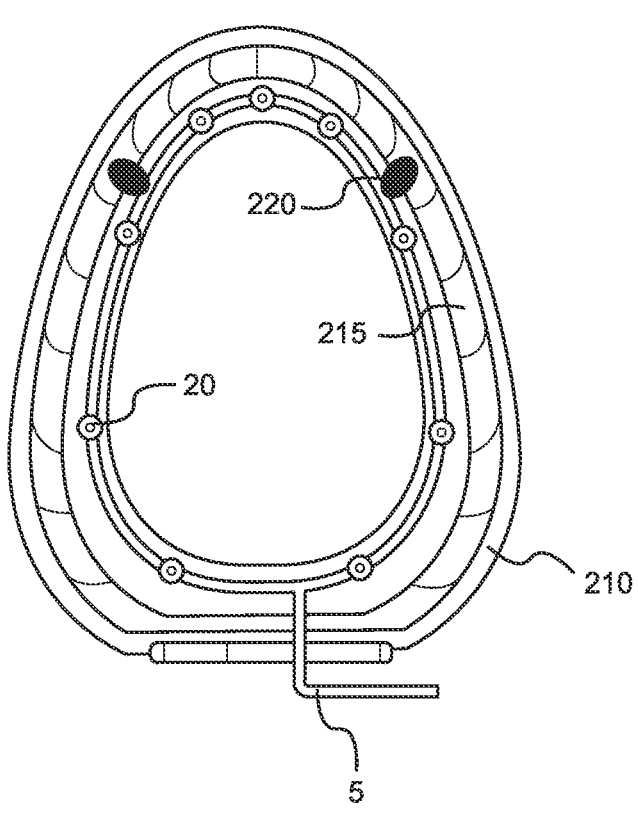
FIG. 2*a* is a bottom plan view of a disinfecting fluid delivery system mounted on a toilet seat in accordance with some embodiments of the presently disclosed subject matter.
Figure 2B:
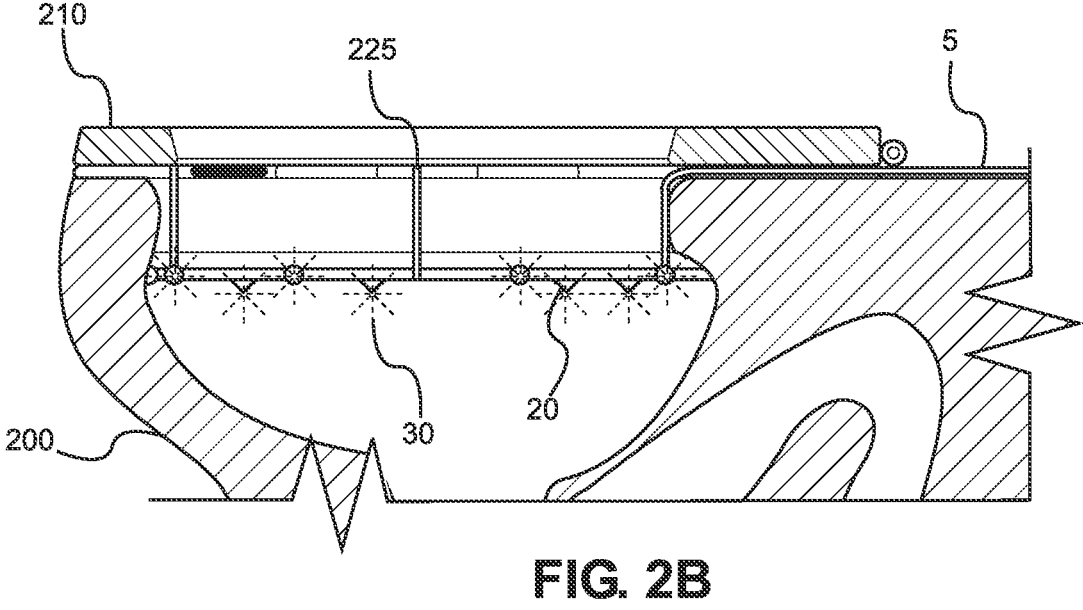
FIG. 2*b* is a side plan view of a disinfecting fluid delivery system mounted on a toilet bowl in accordance with some embodiments of the presently disclosed subject matter.

FIGS. 2a and 2b depict one embodiment of a disinfecting fluid delivery system mounted on a toilet bowl 200. In this embodiment, a disinfecting fluid delivery header 5 delivers disinfecting fluid 30 to a toilet. The header is mounted in this embodiment on the bottom of the toilet seat 210 and is designed to hang down from supports 225 to the degree needed to best position the fluid spray nozzles 20. As in most all toilet bowl seats, load bearing feet 220 are provided underneath the seat that are in contact with the toilet bowl upper rim. To prevent disinfecting fluid from spraying out between the bottom of the toilet seat and the top of the rim, a ring of material 215 is provided to block fluid. This ring of material 215 may be made of soft material so as to conform to varying gap distances. In FIG. 2a, the fluid blocking material is mounted on the underside of the toilet seat. In other embodiments, it may be mounted on the toilet rim, and may be as simple as a bead of caulk deposited onto the upper edge of the toilet rim. In other embodiments, the fluid header 5 is mounted on the toilet rim and not the seat.

Figure 3A:
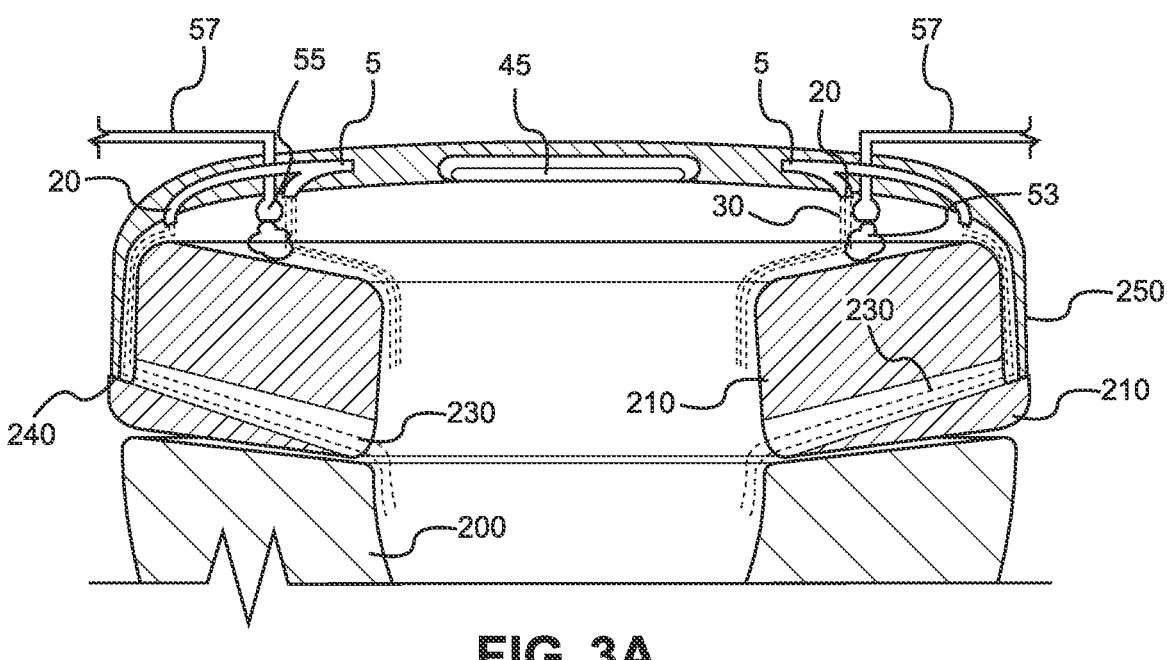
FIG. 3*a* is front plan view of a system for disinfecting a toilet seat in accordance with some embodiments of the presently disclosed subject matter.
Figure 3B:
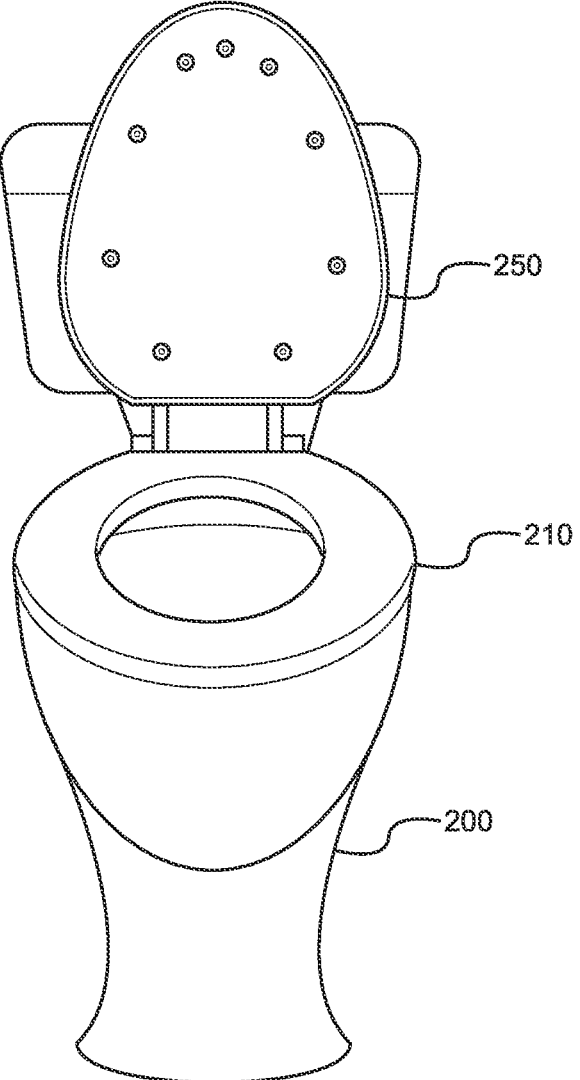
FIG. 3*b* is a perspective view of a system for disinfecting a toilet seat in accordance with some embodiments of the presently disclosed subject matter.

FIGS. 3a and 3b depict a system and method for disinfecting a toilet seat 210 mounted on toilet 200 with disinfecting fluid. In this embodiment, toilet seat cover 250 comprises a fluid delivery header 5, which ideally may deliver disinfecting fluid or in some cases water without a disinfectant added, with nozzles or openings in the header 20 positioned in various places over the toilet seat when the cover 250 is in the lowered position so as to apply disinfecting fluid 30 onto surfaces of the toilet seat 210. In some embodiments, fluid drainage channels 230 are provided in the seat to facilitate draining of fluid that may fall onto the outside of the seat back into the toilet bowl. FIG. 3A depicts the toilet seat cover 250 touching the toilet seat 210 on a lip 240 that extends outward around the bottom portion of the seat and which provides a place for the cover to close onto and make a seal or partial seal against the seat, the purpose of which is to contain disinfecting fluid which may run down the outside of the seat. With the provision of this lip and seal of the cover against this lip, and the channels to drain the fluid back into the toilet bowl, the seat may be more fully sprayed and disinfected while at the same time containing the disinfecting fluid without as much concern of making a mess. In some embodiments, a UV lamp or UV LED 45 may be mounted in the toilet seat cover 250 and configured to emit germicidal UV radiation when the cover is in the lowered position. In some embodiments, a compressed air header 57 is also provided to supply compressed air 53 or heated air from an air compressor or air moving device (not shown) to an air header also mounted in or on the toilet seat cover 250. At various locations above the toilet seat a multiplicity of air nozzles 55 allow compressed air to exit the air header 57 and blow air 53 onto the seat so as to accelerate removal of the fluid from the seat and drying of the seat. In some embodiments, a control system (not shown) is provided that first applies disinfecting fluid to the seat for a period of time, then stops the flow of disinfecting fluid and applies a flow of air to the seat to facilitate drying. In some embodiments, the control system comprises person detection sensors or other sensors such as a flush detection sensor and toilet seat cover position detection sensor to detect when a user has finished using the toilet, whether the toilet seat cover is in a lowered position, and upon determining that the toilet seat cover is in a lowered position, activating a cycle of dispensing disinfecting fluid to the toilet seat followed by optionally applying air to the toilet seat to dry the seat and ready it for the next user. In still further embodiments, a system is provided to automatically raise and lower the toilet seat cover, optionally closing the toilet seat cover and initiating a disinfecting cycle upon determining that a person has finished using the toilet and then raising it again after the cycle has been completed to ready the toilet for the next user.

Figure 4:
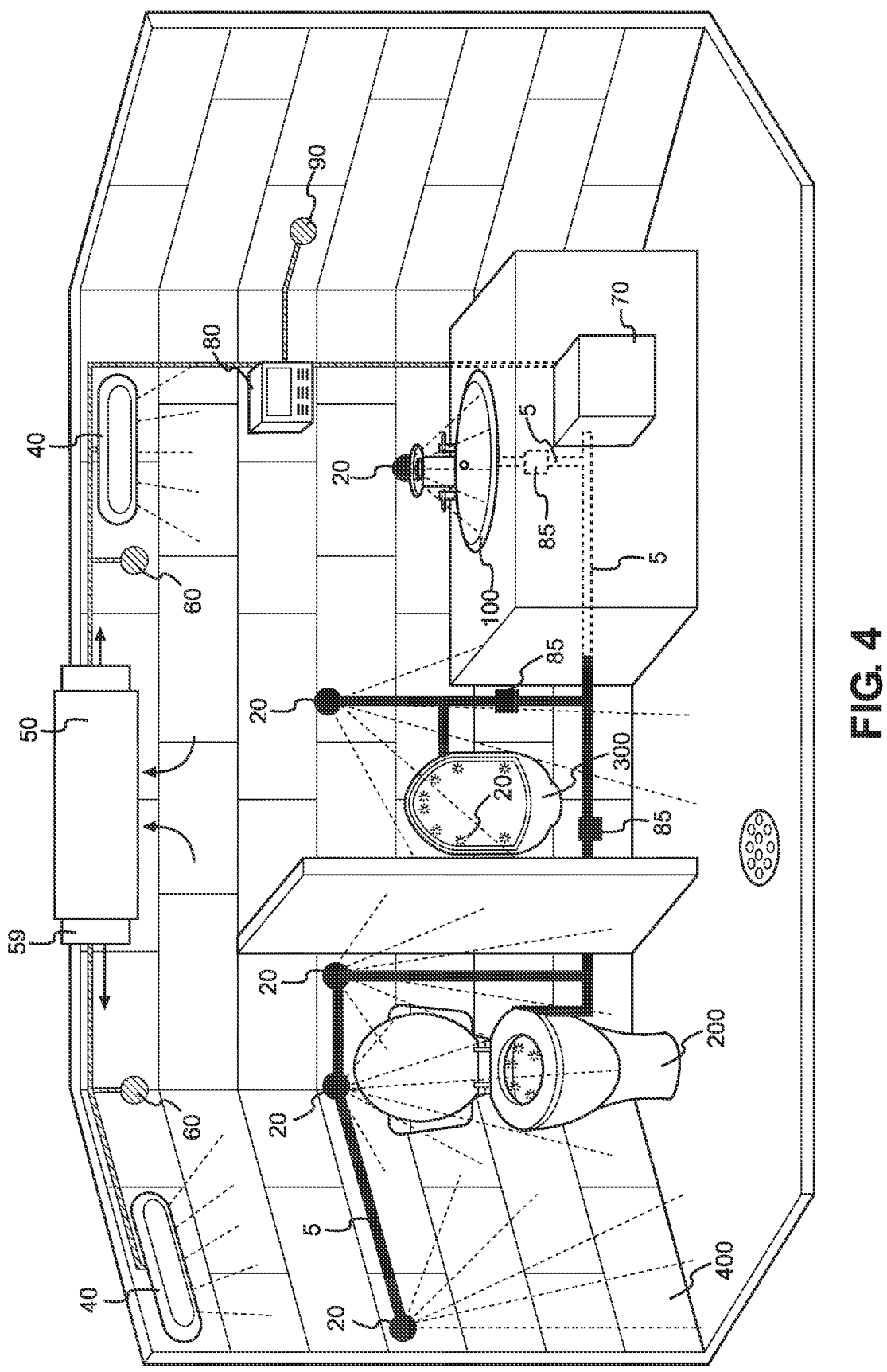
FIG. 4 is a perspective view of a fluid delivery system positioned in a bathroom in accordance with some embodiments of the presently disclosed subject matter.

FIG. 4 depicts a system and method for disinfecting a public restroom, for example a restroom in a school, restaurant, hospital, office building, or retail store. FIG. 4 depicts four plumbing fixtures in the restroom: a sink 100, a toilet 200, a urinal 300, and the walls and floor of the restroom with associated floor drain 400. Fluid delivery system 70, which may comprise a system which generates ozonated water in a cold water supply line, pumps disinfecting fluid through disinfecting fluid header 5 to the various plumbing fixtures and out spray nozzles 20 located at various points along the header and situated to apply disinfecting fluid into or onto the plumbing fixtures, including onto a wall or floor. The walls and floor in this example are tiled or comprise other water-proof materials so as to be readily sprayed with disinfecting fluid without causing damage. A programmable control system 80 is provided and mounted in a convenient place, the control system being configured to receive inputs from person location detectors 60 and chemical and other detectors 90 and control the disinfecting fluid cycles and the operation of UV emitters 40 and air filter 50 in response to determining the presence of a person in the bathroom and other parameters. In this example, a chemical sensor 90 capable of detecting the concentration of the disinfectant, for example ozone, in the air sends signals to the control system 80, and in response to high concentrations of disinfectant in the air, the control system may activate the air moving or air filtration system 50 equipped with canisters 59 of activated carbon to remove ozone from the air. Some embodiments also comprise control valves 85 which are useful to allow the control system to disinfect one plumbing fixture at a time so as to allow a smaller disinfecting fluid system to be used rather than a system sized to disinfect the entire bathroom and all its surfaces at the same time.

In some embodiments, ultraviolet (UV) source (e.g., a low pressure mercury vapor lamp) can be supplied to emit UV radiation. The UV source can be operated when persons are not present and the ozonated water is not being sprayed, thus providing additional disinfection more than what can be achieved by the ozonated water. Suitable wavelengths for pathogen disinfection can be about 240 to 320 nm. If the UV radiation intensity is such that the safety of persons in nearby areas is of concern, a door position sensor can be provided in communication with the UV radiation control system and/or ozonated water control system so that the UV radiation or ozonated water cannot be activated unless both the door is closed and no person is detected in the room or area.

EXAMPLES

Example 1

Disinfecting Three Plumbing Fixtures with 1% Hydrogen Peroxide

An automated plumbing fixture disinfection system was constructed and demonstrated to disinfect a bathroom sink, toilet, and shower in a bathroom in a home. First, a control module or control system was constructed using a Raspberry Pi computer with 7 inch touchscreen monitor, Arduino microcontroller, two electronic breadboards, power supplies, and other electrical interfaces. A computer program written in Python receives inputs from the user via a convenient, single-screen input graphic on the touch screen. The graphic allows the user to independently specify the times that disinfecting fluid is dispensed to the sink, toilet, and shower by pressing up and down keys to increase or decrease minutes and seconds for each time. The time between disinfection cycles or cycle time is also input in the same manner. The graphic allows the chemical pump, 3-MD SC made by Little Giant Pump Co., to be enabled or disabled with the touch of a button. A button to start and stop the disinfecting cycle and also an output telling the user what part of the cycle is being run and how much time is left with that part of the cycle is also provided on the graphic interface screen. Second, the chemical storage and distribution structure or fluid delivery headers were constructed using a 15 gallon polypropylene drum with a suction line feeding the pump, and the pump discharge line feeding a header that then branched first to the shower, then to the toilet, and then to the sink. All chemical lines were made from half inch ID PVC reinforced tubing. Half inch stainless steel ball valves manufactured by U.S. Solid were installed in each branch to each plumbing fixture to control the on/off flow to each plumbing fixture, with the valve electronic actuators being wired to the control module and controlled by the program. The distribution structure conduit or tubing at the plumbing fixtures was customized to the shape and location of each plumbing fixture and was attached to each plumbing fixture in the following manner. Downstream of the sink control valve the tubing branched into two lines, an upper one mounted above the sink's faucet to spray disinfecting fluid onto the faucet and hot and cold water faucet handles, and a lower branch to wrap around the outer perimeter of the sink basin to spray disinfecting fluid down along the sides of the basin. A plexiglass backsplash was constructed about ten inches in height and 14 inches in width, plus partitions on either side protruding forward from the back panel at 45 degrees to help guide disinfecting fluid into the sink basin. The backsplash was held down to the countertop by a bead of silicone caulk, and the upper branch of tubing was mounted on this backsplash above the faucet. The lower tubing was mounted on a plexiglass strip about 1 inch wide and cut in a shape so as to lay on the countertop at the outer edge of the sink bowl and surround the outer perimeter of the sink. Holes were drilled in the tubing into which Quarter Circle Fan Micro Spray nozzles made by Mister Landscaper and available at Lowes were inserted and directed to either spray downward to coat the sink walls directly under the nozzles with disinfecting fluid or outward to spray disinfecting fluid into the sink basin on the opposite side of the sink. Five nozzles were mounted in the lower branch and three in the upper branch, and in this manner virtually 90 to 100% of the surfaces of the sink bowl, including the faucets, were contacted with disinfecting fluid when activated. For the toilet, a ring of half inch tubing was mounted on the lower side of a standard toilet seat. In this tubing, eleven Half Circle Fan Micro Spray nozzles were inserted with ten directed outwards toward the inner surfaces of the toilet bowl and one directed downwards so as to spray fluid onto a relatively large surface of the toilet bowl in the front of the toilet that sloped more gently and was not easily contacted by spray directed towards the sides. For the shower/tub combination, the tubing fed a ¾" CPVC pipe into which five Half Circle spray nozzles were inserted towards the faucet and drain end of the shower and directed towards the front wall and front right wall only in this prototype. One nozzle was oriented downward so as to spray the shower control handle once ATP testing determined that each surface must be directly contacted by the disinfectant in order to be disinfected. Being in close proximity to a nearby surface that is being sprayed is insufficient to disinfect a surface not being sprayed with disinfecting fluid. The program was configured to first apply disinfecting fluid to the sink for the time inputted for the sink, then the toilet, then the shower. When the cycle begins, the program first opens the ball valve to allow fluid to flow to a particular plumbing fixture, and then the pump is turned on and remains on until the end of the dispensing time, at which point the pump is turned off and the valve is closed. This sequence then repeats sequentially until all three plumbing fixtures have received the prescribed time of disinfecting fluid application.

32% hydrogen peroxide was purchased from Lab Alley and diluted to 1% and placed in the 15 gallon storage container. The flow rate to each plumbing fixture was measured or estimated to be about 1 gpm to the toilet and about 0.4 gpm to the shower and about 0.5 gpm to the sink. The reason for the difference in rates has to do with pressure drop through the system, number of holes or nozzles, and height of the plumbing fixture. The toilet for example received so much more flow than the other plumbing fixtures because there were eleven nozzles, it was lowest elevation and therefore substantially less liquid head to overcome by the pump, and it was closest to the pump. The shower on the other hand had the fewest nozzles, highest height, and longest distance from the pump and therefore had the lowest flow. The system may be adjusted to deliver the same flow to each plumbing fixture or different flows, and in this case, the flow of fluid to each fixture during each disinfecting cycle could have easily been made the same by setting for example a longer disinfecting time for the shower and sink than the toilet. In this example, the disinfecting times were all set the same and the flow rates to each were allowed to vary. ATP (adenosine triphosphate) tests were performed to detect the presence of living organisms using Hygiena's SystemSURE Plus ATP monitoring system with their Ultrasnap swabs. The ATP results after about one week of disinfecting each plumbing fixture hourly for 30 or 40 seconds using 1% H2O2 are as follows.

| | Before | After 3.5 Days | After 6.5 days |
|---|---|---|---|
| Inside Toilet Bowl | | | |
| Under Rim, right[1] | 26 | 3 | |
| Bowl Surface (above water), right | 173 | 7 | |
| Under Rim, front[1] | 74 | 15 | 2 |
| Bowl Surface, front | 91 | 21 | 5 |
| Under Rim, left[1] | 258 | 1 | |
| Bowl Surface, left | 81 | 5 | 3 |
| Under Rim, rear[1] | 3083 | 2 | |
| Bowl Surface, rear | 17 | 3 | |
| Shower/Tub | | | |
| Handle | 225 | 5381[2] | 16 |
| Tub Floor, left of drain | 4511 | 38 | |
| Top of Drain Plug and Drain Collar | 6941 | 38 | |
| Tub Floor, right of drain | 6204 | 8 | 22 |
| Inside Drain[1] | 6559 | 6 | |
| Tub Floor Center | 1789 | 557[3] | |
| Shower Sidewall, Tile and Grout | 192 | 3 | |
| Shower Sidewall, Tile and Grout | 156 | 7 | |
| Sink | | | |
| Top of Drain Plug and Drain Collar | 4351 | 46 | |
| Inside Drain Collar Wall[1] | 1951 | 10 | |
| Drain Plug, Down Inside Drain[1] (avg) | 6863 | 95 | |
| Sink Basin, Right of Drain | 770 | 13 | |
| Sink Counter, left of faucet | 1876 | 6 | |

Values shown are ATP results reported in RLU units measured with Hygiena SystemSure Plus.
Disinfecting fluid was 1% H₂O₂ applied to each fixture for 40 secs each hour for 3.5 days then for 30 s each hour for another 3 days.
Notes: 1. Typically very high bioburden and inaccessible to std cleaning methods. These are very promising results. 2.

Disinfectant missed handle until adjustments were made to allow disinfecting spray to hit handle (handle had serrated, difficult-to-clean crevices). 3. This data point remained high due to soap scum not being removed.

Example 2

Disinfecting Three Plumbing Fixtures with 1% Hydrogen Peroxide, UV Radiation, and Room Air Purification The system of Example 1 was further configured to add UV emitting lamps with motion detectors and door sensors to the control module electronic inputs and outputs and to touch screen control graphic. Three PID motion detectors were mounted at various points in the bathroom, including one with a view to the shower area, with hardwiring input to the control module. In addition, two door position sensors, each comprising two pieces, one mounted on the bathroom door and one mounted on the door jam, were added to the system and also hardwired into the control module. The program was configured to not allow power to the UV lamps when any three of the following events are true: the door is open as determined by either of the two door contacts, motion is detected by any of the three motion detectors, or the system was dispensing disinfecting chemicals onto a plumbing fixture. If all of those three conditions were false, and the button on the touch screen entitled "Enable UV" was touched, then the system would turn on electrical power to a duplex receptacle. A floor lamp with three light bulb sockets and an extension cord ending in a single light bulb socket were both plugged into this receptacle. Four 25W UVC light bulbs emitting germicidal radiation capable of killing microorganisms marketed under the name Coospider and made by Aopu Light (JY) Co. Ltd. were screwed into the floor lamp light bulb sockets and the extension cord socket. The light bulb on the extension cord was located five feet away from the floor lamp to allow UVC radiation to directly illuminate surfaces of the plumbing fixtures and other surfaces in the room that the bulbs in the floor lamp could not, which is referred to herein as distributed emissions of UV radiation. Distributed UV emissions is a key to effectively disinfecting a room with radiation, since shadow areas where the light from a single source cannot reach are a major drawback to UV disinfection. In addition to the UV lamps and hydrogen peroxide solution being periodically and automatically dispensed in the three plumbing fixtures, an free standing air filter model Core 400S made by Levoit comprising a HEPA filter element and an activated carbon element to remove chemical vapors and odors from the air was placed in the bathroom and turned on high. After initiating the control module on the touchscreen and exiting the room, the UV lamps came on to emit disinfecting UV radiation when the fluid was not being dispensed in the plumbing fixtures. Thus, the air in the bathroom was being purified by the air filter and the activated carbon element in the air filter, the air and surfaces in the bathroom were being disinfected by the UVC radiation being emitted, and periodically the plumbing fixtures were being disinfected by the application of 1% hydrogen peroxide. Although not done for this example, it is obvious that with simple additional changes to the control module, an air filter may also be configured to be controlled by the same control module and touch screen used for chemical dispensing and UV emitting.

Example 3

Disinfecting Plumbing Fixtures with Ozonated Water

A system capable of making 1.5-2.0 gallons per minute (GPM) of 2-3 ppm ozone dissolved in water fed from a standard house cold water supply line, model AOS-2 from Oxidation Technologies, LLC in Inwood, IA, was acquired and installed the bathroom of Example 1. Four ozone sensors located at various points in the bathroom were hardwired to the control module of Example 1, with the ozone concentration from each being displayed on a local website and viewable on computers in nearby rooms outside the bathroom. The control module and fluid delivery header and structure described in Example 1 were used to deliver ozonated water to the plumbing fixtures. However, the spray nozzles described in Example 1 created too much back pressure and prevented the unit from operating properly, so the nozzles were replaced by tubing that simply had holes drilled in it for the ozonated water to run out and onto the plumbing fixture surfaces. This resulted in less than idea coverage of some of the fixture surfaces with ozonated water, but where there was wetting of the surfaces, one to two orders of magnitude, sometimes better, of disinfection as measured by the ATP method was observed after about a week of applying ozonated water for five minutes every hour, twenty-four hours a day. The ozone generating system was turned on and in standby at all times, and when the control module called for a fluid dispensing event to a plumbing fixture and opened the appropriate valve to a particular fixture, this allowed water from the water supply line to flow through the ozone unit to the fixture's fluid delivery structure. The movement of water through the venturi in the ozone unit then pulled a vacuum on the line from the ozone generator, which in turned caused the ozone generator to turn on and draw ozonated air into the water. After separating the ozonated air from the water and venting the excess ozonated air, the water flowing through the system comprised about 2-3 ppm ozone. The air filter with carbon in example 2 was operated during testing with the ozone system, thereby removing some ozone from the air. The UV system described in Example 2 was also at times operated during the ozonated water tests. It is believed that with a different ozonated water generating unit, for example one with a pump located on the discharge, higher flow rates and better coverage of the fixture surfaces will be readily obtained.

Example 4

Ozonated Water on Heavy Contamination

A wall of the tub and shower was allowed to become heavily contaminated with black mold and mildew, heavily darkening tiles, tub surfaces, grout, and caulk. The ozonated water generator of Example 3 was operated with the full discharge flow split into two discharge lines each aimed at different parts of the shower/tub, one on the tiled wall on the side of the shower and one on the tub surfaces. Each line was held in a fixed position where the ozonated water made a definitive stream path, either against and down the wall or onto a surface in the tub. The programmable controller was set to allow ozonated water to flow for 55 minutes every hour. After 10 hours of continuous operation in this manner, it was very obvious where the ozonated water paths had been, particularly on the shower wall and tile areas, as the mildew and mold had been almost entirely removed on the tile and tile grout areas, and everywhere the ozonated water had been impinging on the wall and tub, the black mold and mildew had been markedly lightened, including in the grout and caulk lines, places that are notoriously difficult to whiten. Remarkably, the ATP measurements on four areas of the whitened wall tiles showed an average of 249 RLU's compared to 6872 RLU's on the tiles just a few inches away where the ozonated water did not contact. During the operation of the ozonated water generation unit, ozone could be smelled in the room, and a Febreze Light Plug distributed by Proctor and Gamble was used to emit fresh smelling odors into the room which also may react with the ozone to decrease the amount of ozone in the air.

What is claimed is:

1. A system for disinfecting at least one plumbing fixture, the system comprising:
   at least one plumbing fixture located in a room comprising a bathroom in a building;
   a disinfecting chemical storage or disinfecting chemical generation unit for storing, generating, or both storing and generating a disinfecting fluid;
   a programmable control module or manual controls for inputting, adjusting, or both inputting and adjusting system control parameters;
   a distribution structure comprising piping or other conduit fixedly mounted relative to the plumbing fixture and configured to pump or convey the disinfecting fluid to a surface of the plumbing fixture;
   an attachment configured to attach a portion of the distribution structure piping or other conduit on, in, or near the plumbing fixture;
   at least two separate openings integrally formed in the piping or other conduit, wherein each of the at least two separate openings is configured to distribute the disinfecting fluid onto a different area on a surface of the plumbing fixture surface relative to the remaining openings, the at least two separate openings being physically spaced apart along the piping or other conduit and positioned and oriented to direct disinfecting fluid toward different predetermined surface regions of the plumbing fixture.

2. The system for disinfecting at least one plumbing fixture of claim 1, wherein the system comprises at least three, four, five, six, seven, eight, nine, or ten openings.

3. The system for disinfecting at least one plumbing fixture of claim 1, wherein the plumbing fixture is selected from a sink, a toilet, a bathtub, a shower, or a portion of a wall or floor of the room equipped with a floor drain.

4. The system for disinfecting at least one plumbing fixture of claim 1, wherein the system is configured to disinfect either simultaneously or sequentially two or more plumbing fixtures wherein the two or more plumbing fixtures are the same type of plumbing fixture or are different types of plumbing fixtures.

5. The system for disinfecting at least one plumbing fixture of claim 1, wherein a portion of the distribution structure is positioned into a new plumbing fixture.

6. The system for disinfecting at least one plumbing fixture of claim 1, wherein a portion of the distribution structure is configured to apply the disinfecting fluid onto at least one faucet, handle, or other high touch point of the at least one plumbing fixture.

7. The system for disinfecting at least one plumbing fixture of claim 1, further comprising a backsplash or other barrier to control the direction of flow of the disinfecting fluid and to prevent the disinfecting fluid from contacting non-plumbing fixture surfaces or surfaces of the at least one plumbing fixture not intended to be regularly wetted with fluids.

8. The system for disinfecting at least one plumbing fixture of claim 1, wherein a portion of the distribution structure is configured to apply the disinfecting fluid onto at least 10%, 20%, 30%, 40%, 50%, 60%, 70%, 80%, or 90% of a surface of the at least one plumbing fixture intended to be regularly wetted with fluids.

9. The system for disinfecting at least one plumbing fixture of claim 1, wherein the disinfecting fluid comprises ozone.

10. The system for disinfecting at least one plumbing fixture of claim 1, wherein the disinfecting chemical storage unit stores a disinfecting chemical chosen from hydrogen peroxide, a chemical comprising chlorine, or a chemical comprising a quaternary ammonium compound.

11. The system for disinfecting at least one plumbing fixture of claim 1, further comprising at least one germicidal radiation emitter including a UV emitter.

12. The system for disinfecting at least one plumbing fixture of claim 11, further comprising a person detection sensor, a door position detection sensor, or both.

13. The system for disinfecting at least one plumbing fixture of claim 11, comprising a plurality of germicidal radiation emitters wherein each of the germicidal radiation emitters are located at least one, two, three, four, five, six, eight, or ten feet apart from another germicidal radiation emitter.

14. The system for disinfecting at least one plumbing fixture of claim 11, further comprising an air movement element configured to move air in the room, the air movement element comprising an air filter equipped with a fan to circulate air through the air filter.

15. The system for disinfecting at least one plumbing fixture of claim 14, further comprising a programmable control module configured to control components of the air movement element, the germicidal radiation emitter, the distribution structure, the air filter, or combinations thereof.

16. The system for disinfecting at least one plumbing fixture of claim 1, further comprising an air movement element configured to move air in the room, the air movement element comprising an air filter equipped with a fan to circulate air through the air filter.

17. The system for disinfecting at least one plumbing fixture of claim 16, further comprising a compound for absorbing or destroying an airborne disinfecting chemical, including ozone, a sensor to detect compounds in the air, including a disinfecting chemical, or both.

18. The system for disinfecting at least one plumbing fixture of claim 1, wherein a portion of the distribution structure is configured to apply the disinfecting fluid onto a toilet seat.

19. The system for disinfecting at least one plumbing fixture of claim 18, further comprising an air movement element configured to move air onto the toilet seat.

20. A facility selected from a healthcare facility, nursing home, rehabilitation or long-term care facility, restaurant, office building, school, retail store, hotel, hospitality facility, auditorium, theater, recreational facility including a gymnasium, stadium, swimming pool, fitness center, food processing or preparation facility, research facility, manufacturing facility, private restroom, or public restroom, the facility comprising:

at least one bathroom comprising at least one plumbing fixture;

a disinfecting chemical storage or disinfecting chemical generation unit configured for storing, generating, or both storing and generating a disinfecting fluid;

a programmable control module or manual controls for inputting, adjusting, or both inputting and adjusting system control parameters;

a distribution structure comprising piping or other conduit fixedly mounted relative to the plumbing fixture and configured to pump or convey the disinfecting fluid to a surface of the at least one plumbing fixture;

an attachment configured to attach a portion of the distribution structure piping or other conduit on, in, or near the at least one plumbing fixture;

at least two separate openings integrally formed in the piping or other conduit configured to distribute the disinfecting fluid onto different areas of a surface of the at least one plumbing fixture, the at least two separate openings being physically spaced apart along the piping or other conduit and positioned and oriented to direct disinfecting fluid toward different predetermined surface regions of the plumbing fixture.

* * * * *